(12) United States Patent
Sarubbi

(10) Patent No.: US 8,785,381 B2
(45) Date of Patent: Jul. 22, 2014

(54) ORAL GLP-1 FORMULATIONS

(75) Inventor: Donald J. Sarubbi, Hartsome, NY (US)

(73) Assignee: Emisphere Technologies, Inc., Roseland, NJ (US)

( * ) Notice: Subject to any disclaimer, the term of this patent is extended or adjusted under 35 U.S.C. 154(b) by 211 days.

(21) Appl. No.: 12/497,373

(22) Filed: Jul. 2, 2009

(65) Prior Publication Data

US 2010/0016229 A1    Jan. 21, 2010

Related U.S. Application Data

(63) Continuation of application No. 11/018,180, filed on Dec. 20, 2004, now abandoned.

(60) Provisional application No. 60/552,116, filed on Mar. 10, 2004, provisional application No. 60/530,931, filed on Dec. 19, 2003.

(51) Int. Cl.
*A61K 38/28* (2006.01)
*C07C 229/00* (2006.01)

(52) U.S. Cl.
USPC ............................. 514/5.9; 514/563; 562/444

(58) Field of Classification Search
None
See application file for complete search history.

(56) References Cited

U.S. PATENT DOCUMENTS

| | | |
|---|---|---|
| 5,118,666 A | 6/1992 | Habener |
| 5,120,712 A | 6/1992 | Habener |
| 5,122,539 A | 6/1992 | Abraham et al. |
| 5,238,917 A | 8/1993 | Fujii et al. |
| 5,304,575 A | 4/1994 | Beck |
| 5,424,286 A | 6/1995 | Eng |
| 5,443,841 A | 8/1995 | Milstein et al. |
| 5,447,728 A | 9/1995 | Milstein et al. |
| 5,451,410 A | 9/1995 | Milstein et al. |
| 5,512,549 A | 4/1996 | Chen et al. |
| 5,541,155 A | 7/1996 | Leone-Bay et al. |
| 5,545,618 A | 8/1996 | Buckley et al. |
| 5,578,323 A | 11/1996 | Milstein et al. |
| 5,614,492 A | 3/1997 | Habener |
| 5,629,020 A | 5/1997 | Leone-Bay et al. |
| 5,631,224 A | 5/1997 | Efendic et al. |
| 5,643,957 A | 7/1997 | Leone-Bay et al. |
| 5,650,386 A | 7/1997 | Leone-Bay et al. |
| 5,693,338 A | 12/1997 | Milstein |
| 5,705,483 A | 1/1998 | Galloway et al. |
| 5,714,167 A | 2/1998 | Milstein et al. |
| 5,734,026 A | 3/1998 | Florin-Robertsson et al. |
| 5,766,620 A | 6/1998 | Heiber et al. |
| 5,766,633 A | 6/1998 | Milstein et al. |
| 5,773,647 A * | 6/1998 | Leone-Bay et al. ........... 562/444 |
| 5,780,599 A | 7/1998 | Junker et al. |
| 5,792,451 A | 8/1998 | Sarubbi et al. |
| 5,811,127 A | 9/1998 | Milstein et al. |
| 5,820,881 A | 10/1998 | Milstein |
| 5,837,702 A | 11/1998 | Rovnyak et al. |
| 5,849,322 A | 12/1998 | Ebert et al. |
| 5,863,555 A | 1/1999 | Heiber et al. |
| 5,866,536 A | 2/1999 | Leone-Bay et al. |
| 5,935,601 A | 8/1999 | Leone-Bay et al. |
| 5,955,503 A | 9/1999 | Leone-Bay et al. |
| 5,958,457 A | 9/1999 | Santiago et al. |
| 5,965,121 A | 10/1999 | Leone-Bay et al. |
| 5,976,569 A | 11/1999 | Milstein |
| 5,977,071 A | 11/1999 | Galloway et al. |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,006,753 A | 12/1999 | Efendic |
| 6,009,856 A | 1/2000 | Smith, III et al. |
| 6,071,510 A | 6/2000 | Leone-Bay et al. |
| 6,071,538 A | 6/2000 | Milstein et al. |
| 6,099,856 A | 8/2000 | Milstein et al. |
| 6,100,298 A | 8/2000 | Leone-Bay et al. |
| 6,180,140 B1 | 1/2001 | Leone-Bay et al. |
| 6,191,102 B1 | 2/2001 | DiMarchi et al. |
| 6,221,367 B1 | 4/2001 | Milstein et al. |
| 6,242,495 B1 | 6/2001 | Leone-Bay et al. |
| 6,245,359 B1 | 6/2001 | Milstein et al. |
| 6,268,343 B1 | 7/2001 | Knudsen et al. |
| 6,284,725 B1 | 9/2001 | Coolidge et al. |
| 6,284,727 B1 | 9/2001 | Kim et al. |
| 6,313,088 B1 | 11/2001 | Leone-Bay et al. |
| 6,329,336 B1 | 12/2001 | Bridon et al. |
| 6,344,213 B1 | 2/2002 | Leone-Bay et al. |
| 6,346,242 B1 * | 2/2002 | Leone-Bay et al. ......... 424/85.1 |
| 6,380,357 B2 | 4/2002 | Hermeling et al. |
| 6,428,780 B2 | 8/2002 | Leone-Bay et al. |

(Continued)

FOREIGN PATENT DOCUMENTS

EP    619322 A2    10/1994
EP    0658568 A1    6/1995

(Continued)

OTHER PUBLICATIONS

Baughman et al, Circulation, 98: 1610-1615, 1998.*
Aungst, BJ, "Novel Formulation Strategies for Improcing Oral Bioavailability of Drugs with Poor Membrane Permeation or Presystemic Metabolism", Jour. Pharm. Science, 1993, pp. 979-987, vol. 82(10).
Epand, R. M., Mol. Pharmacol., 22:105-108, 1982.

(Continued)

*Primary Examiner* — Gyan Chandra
(74) *Attorney, Agent, or Firm* — Blank Rome LLP

(57) ABSTRACT

The present invention provides pharmaceutical compositions comprising of at least one delivery agent and GLP-1. These pharmaceutical compositions facilitate the oral delivery of GLP-1, providing improved (e.g. increased) bioavailability of GLP-1 compared to administration of GLP-1 without a delivery agent.

6 Claims, No Drawings

(56) References Cited

U.S. PATENT DOCUMENTS

| | | | |
|---|---|---|---|
| 6,461,643 | B2 | 10/2002 | Milstein et al. |
| 6,514,500 | B1 | 2/2003 | Bridon et al. |
| 6,555,521 | B2 * | 4/2003 | Hermeling et al. ............. 514/12 |
| 6,583,111 | B1 | 6/2003 | DiMarchi et al. |
| 6,642,411 | B1 * | 11/2003 | Leone-Bay et al. .......... 562/455 |
| 6,646,162 | B2 | 11/2003 | Tang et al. |
| 2003/0225300 | A1 * | 12/2003 | Leone-Bay et al. .......... 562/512 |
| 2004/0147484 | A1 | 7/2004 | Boyd et al. |
| 2005/0148497 | A1 | 7/2005 | Khan |
| 2006/0286129 | A1 | 12/2006 | Sarubbi |
| 2009/0286735 | A1 | 11/2009 | Khan et al. |
| 2010/0016229 | A1 | 1/2010 | Sarubbi |

FOREIGN PATENT DOCUMENTS

| | | |
|---|---|---|
| EP | 0869135 A1 | 10/1998 |
| WO | WO-9325579 A1 | 12/1993 |
| WO | WO-9505848 A1 | 3/1995 |
| WO | WO-9620005 A1 | 7/1996 |
| WO | WO-9630036 A1 | 10/1996 |
| WO | WO-9715296 A1 | 5/1997 |
| WO | WO-9805351 A1 | 2/1998 |
| WO | WO-9808531 A1 | 3/1998 |
| WO | WO-9808871 A1 | 3/1998 |
| WO | WO-9819698 A1 | 5/1998 |
| WO | WO-9820895 A1 | 5/1998 |
| WO | WO-9907404 A1 | 2/1999 |
| WO | WO-9916427 A1 | 4/1999 |
| WO | WO-9925727 A2 | 5/1999 |
| WO | WO-9925728 A1 | 5/1999 |
| WO | WO-9940788 A1 | 8/1999 |
| WO | WO-9943708 A1 | 9/1999 |
| WO | WO-9964060 A1 | 12/1999 |
| WO | WO-0007617 A1 | 2/2000 |
| WO | WO-0016797 A2 | 3/2000 |
| WO | WO-0040203 A2 | 7/2000 |
| WO | WO-0047188 A1 | 8/2000 |
| WO | WO-0050386 A1 | 8/2000 |
| WO | WO-0059863 A1 | 10/2000 |
| WO | WO-0132130 A2 | 5/2001 |
| WO | WO-0144199 A1 | 6/2001 |
| WO | WO-0151454 A1 | 7/2001 |
| WO | WO-0202509 A1 | 1/2002 |
| WO | WO-02100338 A2 | 12/2002 |
| WO | WO-03045306 A2 | 6/2003 |
| WO | WO-03072195 A2 | 9/2003 |
| WO | WO-2004062587 A2 | 7/2004 |

OTHER PUBLICATIONS

Final Office Action dated Sep. 22, 2010, issued in U.S. Appl. No. 12/421,590.

Flint, A., et al., J. Clin. Invest., 101:515-520, 1998.

Gutniak, M., et al., N. E. J. Med., 326(20):1316-1322, 1992.

Hermann C., et al., Glucagon-like Peptide-1 and glucose-dependent insulin-releasing polypeptide levels in response to nutrients, Digestion 1995, vol. 56, No. 2, pp. 117-126.

Holz, G. G., et al., Nature, 361:362-365, 1993.

Kim, Y., et al., Pharm. Res., 12:1664-1670, The Application of Crystal Soaking Technique to Study the Effect of Zinc and Cresol on Insulinotropin Crystals Grown from a Saline Solution, 1995.

Komatsu, R., et al., Diabetes, 38:902-905, 1989.

Larsen, MD, Jens, et al., Glucagon-Like Peptide-1 Infusion Must be Maintained for 24 h/day to Obtain Acceptable Glycemia in Type 2 Diabetic Patients Who are Poorly Controlled on Sulphonylurea Treatment, Diabetes Care, vol. 24, No. 8, Aug. 2001, pp. 1416-1421.

Leone-Bay, A, et al., "4-(4-Salicyloylaminophenyl)butryic Acids as a Novel Oral Delivery Agent for Recombinant Human Growth Hormone", Abstracts of AM. Chem. Soc., 1996, pp. 1-2, pMEDI6.

Leone-Bay, A, et al., "4-[4-[(2-Hydroxybenzoyl)amino]phenyl]butyric Acid as a Novel Oral Delivery Agent for Recombinant Human Growth Hormone", J. Med. Chem., 1996, pp. 2571-2578, vol. 39.

Leone-Bay, A, et al., "Delivery Agents that facilitate the absorpotion of macromolecular drugs", Curr. Opinion in Drug Discovery and Dev., 1999, pp. 26-32, vol. 2(1).

Leone-Bay, A, et al., "N-Acylated α-Amino Acids as novel Oral Delivery Agents for Proteins", J. Med. Chem., 1995, pp. 4263-4269, vol. 38.

Leone-Bay, A, et al., "Oral Delivery of Biologically Active Parathyroid Hormone", Pharm. Research, 2001, pp. 964-970, vol. 18(7).

Lone Pridal, et al., International Journal of Pharamceutics, 136:53-59, Absorpotion of glucagon-like peptide-1 can be protracted by zinc or protamine, 1996.

Majsov, S., Int. J. Peptide Protein Res., 40-:33-343, 1989.

Mentlein, R, et al., "Dipeptidyl-peptidase IV hydrolyses gastric inhibitory polypeptide, gluacgons-like peptide-1(7-6)amide, peptide histidine methionine and is responsible for their degradation in human serum", Eur. J. Biochem., 1993, pp. 829-835, vol. 214.

Mentlein, R., et al., Eur. J. Biochem., 214:829-835, 1993.

Murakami, T, et al., "Effect of Absorporation Promoters on Subcutaneous Absorption of Human Epidermal Growth Factor in Rats," J. Pharm. Sciences, 1993, pp. 236-239, vol. 82(3).

Naslund, E. et al., Am. J. Clin. Nutr., 68:525-530, 1998.

Naslund, E., et al., Drug News Perspect, 11:92-97, 1998.

Nauck, M. a., et al., Diabestologia, 36:741-744, 1993.

Nauck, M. A., et al., J. Clin. Invest., 91:301-307, 1993.

Non-Final Office Action dated Mar. 31, 2010, issued in U.S. Appl. No. 12/421,590.

Orskov, C., Diabestologia, 35: 701-711, 1992.

Orskov, C., et al., J. Biol. Chem., 264(22): 12826-12829, 1989.

Rai et al. Actions of Helodermatidae venom peptides and mammalian glucagon-like peptides on gastric chief cells. Am. Physiol J. 1993, vol. 265, pp. G118-G125, see especially abstract and p. G118.

Stoll, BR, et al., "A mechanistic analyssi of carrier-mediated oral delivery of protein therapeutics", J. Controlled Release, 2000 pp. 217-228, vol. 64.

Supplementary European Search Report for EP03707669, dated Jul. 23, 2009.

Suzuki, S., et al., Endocrinology, 125:3109-3114, 1990.

Thorens, B., et al., Diabetes, 42:1219-1225, 1993.

Wang, W., "Oral Protein Drug Delivery", J. Drug Targeting, 1996, pp. 195-232, vol. 4(4).

Baughman et al., Oral Delivery of Anticoagulant Doses of Heparin, Circulation, 98: 1610-1615, 1998.

\* cited by examiner

ORAL GLP-1 FORMULATIONS

CROSS-REFERENCE TO PRIOR APPLICATIONS

This application is a continuation application of U.S. application Ser. No. 11/018,180, filed Dec. 20, 2004, now abandoned, and claims the benefit of U.S. Provisional Application No. 60/552,116, filed Mar. 10, 2004, and U.S. Provisional Application No. 60/530,931, filed Dec. 19, 2003. Each of these applications are hereby incorporated by reference in their entirety.

FIELD OF THE INVENTION

The present invention relates to a formulation comprising a delivery agent and a glucagon-like peptide 1 or a glucagon-like peptide 1 analog compound (collectively "GLP-1"). These formulations are useful as oral medicaments for the treatment of type 2 diabetes and obesity as well as other conditions know to be treated with GLP-1.

BACKGROUND OF THE INVENTION

Type 2 diabetes, also known as non-insulin dependent diabetes mellitus (NIDDM), is a condition in which patients generate insulin, but the insulin cannot be used effectively by the body's cells. This is primarily because the amount of insulin produced in response to rising blood sugar levels is not sufficient to allow cells to efficiently take up glucose and thus, reduce blood sugar levels.

Glucagon-like 1 peptides and glucagon-like 1 peptide analogs (collectively GLP-1) are a potential treatment for type 2 diabetes and obesity. GLP-1 induces the secretion and production of insulin, effectively reducing blood glucose levels in diabetic patients. GLP-1 also inhibits glucagon secretion, inhibits gastric emptying, enhances glucose utilization, and induces weight loss. GLP-1 may also act to prevent the B cell deterioration that occurs as diabetes progresses.

Development of an oral GLP-1 therapeutic has been extremely difficult. This is primarily due to the in vivo instability of the peptide. The high acid content and ubiquitous digestive enzymes of the digestive tract will often degrade GLP-1 before reaching the desired site of absorption. Further, GLP-1 may encounter difficulty in traversing the cells of the epithelial membrane in the small intestine to reach the bloodstream. Also, GLP-1 only remains in solution under a narrow set of conditions.

In light of the above difficulties, oral administration of GLP-1 compounds has not been feasible. GLP-1 compounds are customarily delivered by subcutaneous injection or through continuous subcutaneous infusion or continuous intravenous administration. Because patients are generally adverse to injections and time consuming infusions, patient compliance with GLP-1 administration regimens will be low.

Delivery agent molecules that interact with various active agents compounds in a non-covalent fashion to allow the compounds to cross gut membranes and yet remain therapeutically active have been disclosed in U.S. Pat. Nos. 6,663,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 5,541,155, 5,693,338, 5,976,569, 5,643,957, 5,955,503, 6,100,298, 5,650,386, 5,866,536, 5,965,121, 5,989,539, 6,001,347, 6,071,510, and 5,820,881; U.S. Published Application Nos. 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, 20010003001; and International Published Application Nos. 2003/057650, 2003/057170, 2003/045331, 2003/045306, 2003/026582, 2002/100338, 2002/070438, 2002/069937, 02/20466, 02/19969, 02/16309, 02/15959, 02/02509, 01/92206, 01/70219, 01/51454, 01/44199, 01/34114, 01/32596, 01/32130, 00/07979, 00/59863, 00/50386, 00/47188, 00/40203, 96/30036.

SUMMARY OF THE INVENTION

The present invention provides pharmaceutical compositions comprising at least one delivery agent and GLP-1. These pharmaceutical compositions facilitate the oral delivery of GLP-1, providing an improved (e.g. increased) bioavailability of GLP-1 compared to administration of GLP-1 without a delivery agent. The delivery agent may be selected from the following, including salts thereof:

TABLE 1

| Delivery Agent No. | Compound |
|---|---|
| 1 | 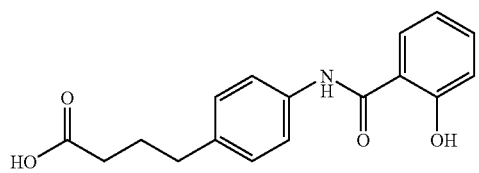 [SMILES: O=C(O)CCCc1ccc(NC(=O)c2ccccc2O)cc1] |
| 2 | 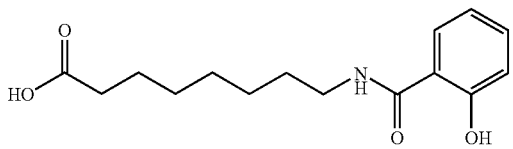 [SMILES: O=C(O)CCCCCCCNC(=O)c1ccccc1O] |

TABLE 1-continued

| Delivery Agent No. | Compound |
|---|---|
| 3 | 4-phenylbutanoyl-NH-C6H4-(CH2)3-COOH |
| 4 | HOOC-CH2-C6H4-NH-CO-C6H4(2-OH) |
| 5 | HOOC-CH2CH2-C6H4-NH-CO-C6H4(2-OCH3) |
| 6 | HOOC-CH(CH3)-C6H4-NH-CO-C6H4(2-OH) |
| 7 | (2-OH, 4-OCH3)-C6H3-CO-NH-(CH2)6-COOH |
| 8 | (4-Cl, 2-OH)-C6H3-CO-NH-(CH2)7-COOH |
| 9 | (2-OH, 5-Br)-C6H3-CO-NH-(CH2)7-COOH |
| 10 | indol-3-yl-(CH2)3-COOH |

TABLE 1-continued

| Delivery Agent No. | Compound |
|---|---|
| 11 | 5-chloro-2-hydroxy-N-(7-carboxyheptyl)benzamide |
| 12 | 3-hydroxy-N-(6-carboxyhexyl)-2-naphthamide |
| 13 | 2,3-dihydroxy-N-(7-carboxyheptyl)benzamide |
| 14 | 2-hydroxy-4-methyl-N-(7-carboxyheptyl)benzamide |
| 15 | 3,5-dichloro-2-hydroxy-N-(7-carboxyheptyl)benzamide |
| 16 | 5-fluoro-2-hydroxy-N-(7-carboxyheptyl)benzamide |
| 17 | 2-hydroxy-5-methoxy-N-(7-carboxyheptyl)benzamide |
| 18 | 3-(2-hydroxybenzamido)propanoic acid |

TABLE 1-continued
| Delivery Agent No. | Compound |
|---|---|
| 19 | 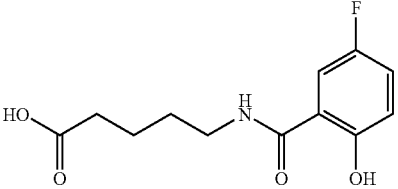 [SMILES: O=C(O)CCCCNC(=O)c1cc(F)ccc1O] |
| 20 | 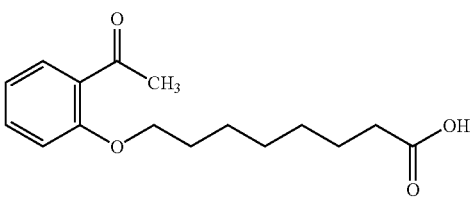 [SMILES: CC(=O)c1ccccc1OCCCCCCCC(=O)O] |
| 21 | 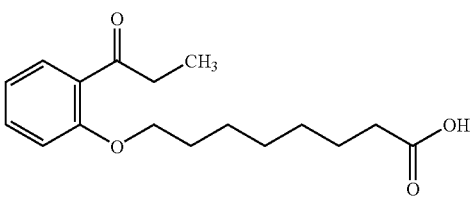 [SMILES: CCC(=O)c1ccccc1OCCCCCCCC(=O)O] |
| 22 | 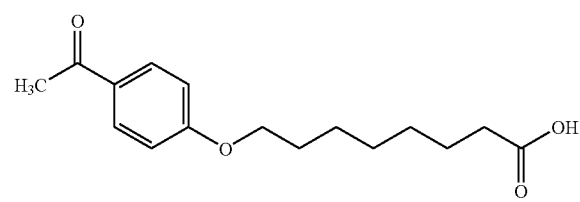 [SMILES: CC(=O)c1ccc(OCCCCCCCC(=O)O)cc1] |
| 23 | 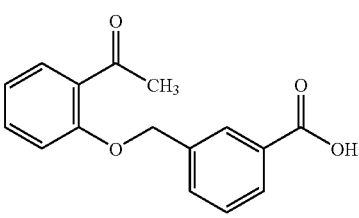 [SMILES: CC(=O)c1ccccc1OCc1cccc(C(=O)O)c1] |
| 24 | 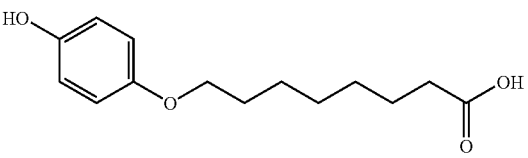 [SMILES: O=C(O)CCCCCCCOc1ccc(O)cc1] |
| 25 | 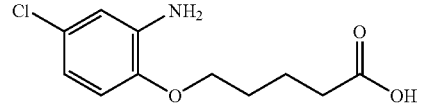 [SMILES: Nc1cc(Cl)ccc1OCCCCC(=O)O] |
| 26 | 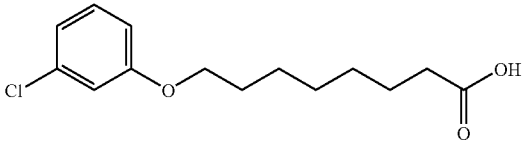 [SMILES: O=C(O)CCCCCCCOc1cccc(Cl)c1] |

TABLE 1-continued

| Delivery Agent No. | Compound |
|---|---|
| 27 | 2-hydroxy-4-chlorobenzamido-pentanoic acid structure |
| 28 | 2-hydroxyphenoxy-heptyl-morpholine structure |
| 29 | 2-hydroxyphenoxy-heptyl-morpholine structure (isomer) |

According to one embodiment, the pharmaceutical composition includes an effective amount of a GLP-1 compound, for example, to treat NIDDM or obesity.

The delivery agents enable the oral delivery of macromolecules, providing an increased or improved bioavailability of GLP-1 compared to administration of GLP-1 without a delivery agent.

Another embodiment is an administration composition that includes at least one delivery agent, GLP-1, and, optionally, a dosing vehicle, an adjuvant, an excipient, or a mixture thereof. The dosage unit form may be a liquid or a solid, such as a tablet, capsule or particles, including a powder or sachet.

Another embodiment is a method for administering GLP-1 to a subject in need thereof by orally administering the pharmaceutical composition of the present invention to the subject.

Yet another embodiment is a method of treating type 2 diabetes or obesity in an animal in need thereof by administering an effective amount of the pharmaceutical composition or dosage unit form of the present invention.

The present invention encompasses the development of novel formulations comprising GLP-1 compounds and delivery agents that can be administered orally. The present invention provides a formulation which can be administered orally comprising a GLP-1 compound and a specified delivery agent. The GLP-1 compound can be native GLP-1; GLP-1 fragments; GLP-1 analogs; GLP-1 derivatives of native, fragments, or analogs of GLP-1; and Exendin-3 and Exendin-4. The delivery agent is selected from delivery agents described in U.S. Pat. Nos. 5,541,155; 5,693,338; 5,976,569; 5,643,957; 5,955,503; 6,100,298; 5,650,386; 5,866,536; 5,965,121; 5,989,539, 6,001,347; 6,071,510; 5,820,881; and 6,242,495; and WO 02/02509; WO 01/51454; WO 01/44199; WO 01/32130; WO 00/59863; WO 00/50386; WO 00/47188; and WO 00/40203.

Preferred GLP-1 compounds are analogs or derivatives of analogs having modifications at one or more of the following positions: 8, 12, 16, 18, 19, 20, 22, 25, 27, 30, 33, and 37 and show increased potency compared with Val$^8$-GLP-1 (7-37)OH.

Preferred GLP-1 compounds are also described in SEQ ID NO.: 1, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10 SEQ ID NO.: 11, SEQ ID NO.: 12, SEQ ID NO.: 13, or SEQ ID NO.: 14. More preferred GLP-1 compounds are described in compounds of SEQ ID NO.: 2, SEQ ID NO.: 12, SEQ ID NO.: 13, and SEQ ID NO.: 14.

Delivery agents are described in Table 1.

The present invention also encompasses a method of stimulating the GLP-1 receptor in a subject in need of such stimulation, said method comprising the step of administering to the subject an effective amount of the oral formulation described herein. Subjects in need of GLP-1 receptor stimulation include those with type 2 diabetes and obesity.

DETAILED DESCRIPTION OF THE INVENTION

The three-letter abbreviation code for amino acids used in this specification conforms with the list contained in Table 3 of Annex C, Appendix 2 of the PCT Administrative Instructions and with 37 C.F.R. 1.822(d)(1) (2000).

Definitions

For purposes of the present invention as disclosed and described herein, the following terms and abbreviations are defined as follows.

The term "formulation" as used herein refers to a GLP-1 compound and a delivery agent combined together which can be administered orally such that the GLP-1 compound passes through the gut into the systemic circulation and has the ability to bind to the GLP-1 receptor and initiate a signal transduction pathway resulting in insulinotropic activity. The formulation can optionally comprise other agents so long as the GLP-1 retains the ability to bind the GLP-1 receptor.

The term "oral" as used herein refers to delivery of a compound by mouth such that the compound passes through the stomach, small intestine, or large intestine into the systemic circulation.

The term "GLP-1 compound" as used herein refers to polypeptides that include naturally occurring GLP-1 polypeptides (GLP-1(7-37)OH and GLP-1(7-36)NH$_2$), GLP-1 fragments, GLP-1 analogs, GLP-1 derivatives of naturally occurring GLP-1 polypeptides, GLP-1 fragments of such derivatives, or GLP-1 analogs of such derivatives, Exendin-3 and Exendin-4, and derivatives thereof, that have the ability to bind to the GLP-1 receptor and initiate a signal transduction pathway resulting in insulinotropic activity.

The term "insulinotropic activity" refers to the ability to stimulate insulin secretion in response to elevated glucose levels, thereby causing glucose uptake by cells and decreased plasma glucose levels. For example, insulinotropic activity can be determined using the method described in Example 1 of International Publication No. WO 03/072195. A GLP-1 molecule has insulinotropic activity if islet cells secrete insulin levels in the presence of the GLP-1 molecule above background levels.

The term "DPP IV resistant" refers to GLP-1 molecules that have extended metabolic stability and improved biological activity. For example, DPP IV resistance can be determined using the method described in Example 2 of International Publication No. WO 03/072195. A GLP-1 molecule is DPP IV resistant if in the presence of DPP IV, the GLP-1 molecule has extended metabolic stability above that of native GLP-1. DPP IV resistant GLP-1 molecules can have an amino acid change at the DPP IV recognition site (position 8), or DPP IV resistant peptides can have an attached group that restricts the accessibility of the DPP IV to the recognition site, or both.

A "GLP-1 fragment" is a polypeptide obtained after truncation of one or more amino acids from the N-terminus and/or C-terminus of GLP-1 (7-37)OH or an analog or derivative thereof. The nomenclature used to describe GLP-1 (7-37)OH is also applicable to GLP-1 fragments. For example, GLP-1 (9-36)OH denotes a GLP-1 fragment obtained by truncating two amino acids from the N-terminus and one amino acid from the C-terminus. The amino acids in the fragment are denoted by the same number as the corresponding amino acid in GLP-1 (7-37)OH. For example, the N-terminal glutamic acid in GLP-1 (9-36)OH is at position 9; position 12 is occupied by phenylalanine; and position 22 is occupied by glycine, as in GLP-1 (7-37)OH. For GLP-1 (7-36)OH, the glycine at position 37 of GLP-1 (7-37)OH is deleted.

A "GLP-1 analog" has sufficient homology to GLP-1 (7-37)OH or a fragment of GLP-1 (7-37)OH such that the analog has insulinotropic activity. Preferably, a GLP-1 analog has the amino acid sequence of GLP-1 (7-37)OH or a fragment thereof modified so that from one, two, three, four or five amino acids differ from the amino acid in corresponding position of GLP-1 (7-37)OH or a fragment of GLP-1 (7-37) OH. In the nomenclature used herein to designate GLP-1 compounds, the substituting amino acid and its position is indicated prior to the parent structure. For example, $Glu^{22}$-GLP-1 (7-37)OH designates a GLP-1 compound in which the glycine normally found at position 22 of GLP-1(7-37)OH has been replaced with glutamic acid; $Val^8$-$Glu^{22}$-GLP-1 (7-37) OH designates a GLP-1 compound in which alanine normally found at position 8 and glycine normally found at position 22 of GLP-1(7-37)OH have been replaced with valine and glutamic acid, respectively.

GLP-1 molecules also include polypeptides in which one or more amino acids have been added to the N-terminus and/or C-terminus of GLP-1 (7-37)OH, or fragments or analogs thereof. It is preferred that GLP-1 molecules of this type have up to about thirty-nine amino acids. The amino acids in the "extended" GLP-1 molecule are denoted by the same number as the corresponding amino acid in GLP-1(7-37)OH. For example, for a GLP-1 molecule obtained by adding two amino acids to the N-terminus of GLP-1(7-37)OH, the N-terminal amino acid is located at position 5; and for a GLP-1 molecule obtained by adding one amino acid to the C-terminus of GLP-1 (7-37)OH, the C-terminal amino acid is located at position 38. Thus, position 12 is occupied by phenylalanine and position 22 is occupied by glycine in both of these "extended" GLP-1 compounds, as in GLP-1 (7-37)OH. Amino acids 1-6 of an extended GLP-1 molecule are preferably the same as or a conservative substitution of the amino acid at the corresponding position of GLP-1 (1-37)OH. Amino acids 38-45 of an extended GLP-1 molecule are preferably the same as or a conservative substitution of the amino acid at the corresponding position of glucagon or Exendin-4.

A "GLP-1 derivative" refers to a molecule having the amino acid sequence of GLP-1, a GLP-1 fragment, or a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ϵ-amino groups, N-alkylation of arginine, histidine, or lysine, alkylation of glutamic or aspartic carboxylic acid groups, and deamidation of glutamine or asparagine.

Modifications of the terminal amino group include, without limitations the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is $C_1$-$C_4$ alkyl. Furthermore, one or more side groups, or terminal groups, may be protected by protective groups known to the ordinarily-skilled protein chemist. The α-carbon of an amino acid may be mono- or dimethylated.

For the purposes of the present invention, an in vitro GLP-1 receptor-signaling assay is used to determine whether a particular extended GLP-1 peptide will exhibit insulinotropic activity in vivo. Extended GLP-1 peptides encompassed by the present invention have an in vitro potency that is not less than one-tenth the in vitro potency of the DPP IV resistant GLP-1 analog known as $Val^8$-GLP-1 (7-37)OH. More preferably, the extended GLP-1 peptides of the present invention are as potent or more potent than $Val^8$-GLP-1 (7-37)OH.

"In vitro potency" as used herein is the measure of the ability of a peptide to activate the GLP-1 receptor in a cell-based assay. In vitro potency is expressed as the "$EC_{50}$" which is the effective concentration of compound that results in 50% activity in a single dose-response experiment. For the purposes of the present invention, in vitro potency is determined using a fluorescence assay that employs HEK-293 Aurora CRE-BLAM cells that stably express the human GLP-1 receptor. These HEK-293 cells have stably integrated a DNA vector having a cAMP response element (CRE) driving expression of the β-lactamase (BLAM) gene. The interaction of a GLP-1 agonist with the receptor initiates a signal that results in activation of the cAMP response element and subsequent expression of β-lactamase. The β-lactamase CCF2/AM substrate that emits fluorescence when it is cleaved by β-lactamase (Aurora Biosciences Corp.) can then be added to cells that have been exposed to a specific amount of GLP-1 agonist to provide a measure of GLP-1 agonist potency. The assay is further described in Zlokarnik, et al. (1998) Science 279: 84-88. Relative in vitro potency values are established by running $Val^8$-GLP-1(7-37)OH as a control and assigning the control a reference value of 1.

The term "delivery agent" refers to molecules in U.S. Pat. Nos. 6,663,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 5,541,155, 5,693,338, 5,976,569, 5,643,957, 5,955,503, 6,100,298, 5,650,386, 5,866,536, 5,965,121, 5,989,539, 6,001,347, 6,071,510, and 5,820,881; U.S. Published Application Nos. 20030232085, 20030225300, 20030198658, 20030133953, 20030078302, 20030072740 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, 20010003001; and International Published Application Nos. 2003/057650, 2003/057170, 2003/045331, 2003/045306, 2003/026582, 2002/100338, 2002/070438, 2002/069937, 02/20466, 02/19969, 02/16309, 02/15959, 02/02509, 01/92206, 01/70219, 01/51454, 01/44199, 01/34114, 01/32596, 01/32130, 00/07979, 00/59863, 00/50386, 00/47188, 00140203, 96/30036, all of which are hereby incorporated by reference. The delivery agents useful in the oral formulations of the present invention. Many of these delivery agents are generally derived from amino acids.

The derived amino acids can also be in the form of poly amino acids, and peptides. An amino acid is any carboxylic acid having at least one free amine group and includes naturally occurring and synthetic amino acids. Poly amino acids are either peptides or two or more amino acids linked by a bond formed by other groups which can be linked, e.g., an ester, anhydride, or an anhydride linkage. Peptides are two or more amino acids joined by a peptide bond. Peptides can vary in length from dipeptides with two amino acids to polypeptides with several hundred amino acids. Preferred peptides include di-peptides, tri-peptides, tetra-peptides, and pentapeptides.

Furthermore, the delivery agents of the present invention are optionally in a salt form. Non-limiting examples of salts include sodium, hydrochloric acid, sulfuric acid, phosphoric acid, citric acid, acetic acid, sulfate, phosphate, chloride, bromide, iodide, acetate, propionate, hydrobromic acid, sodium hydroxide, potassium hydroxide, ammonium hydroxide, and potassium carbonate.

A "Diabetic patient" is a subject having a form of diabetes.

"IGT" refers to impaired glucose tolerance.

"Diabetes" is deemed to encompasses type 1 and type 2 diabetes, unless specifically specified otherwise.

An "effective amount of delivery agent" refers to an amount of the delivery agent that promotes the absorption of a therapeutically effective amount of the drug (i.e., a GLP-1 compound) from the gastrointestinal tract.

"Unit-dose forms" refer to physically discrete units suitable for human and animal subjects and packaged individually as is known in the art. It is contemplated for purposes of the present invention that dosage forms of the present invention comprising therapeutically effective amounts of a GLP-1 compound may include one or more unit doses (e.g., tablets, capsules) to achieve the therapeutic effect.

The term "AUC" as used herein, means area under the plasma concentration-time curve, as calculated by the trapezoidal rule over the complete dosing interval, e.g., 24-hour interval.

The term "$C_{max}$" as it is used herein is the highest plasma concentration of the drug attained within the dosing interval.

The term "$t_{max}$" as it is used herein is the time period which elapses after administration of the dosage form at which the plasma concentration of the drug attains the $C_{max}$ within the dosing interval.

The term "multiple dose" means that the subject has received at least two doses of the drug composition in accordance with the dosing interval for that composition.

The term "single dose" means that the subject has received a single dose of the drug composition or pharmaceutical composition and the drug plasma concentration has not achieved steady state.

Unless specifically designated as "single dose" or at "steady-state" the pharmacokinetic parameters disclosed and claimed herein encompass both single dose and steady-state conditions.

The term "mean", when preceding a pharmacokinetic value (e.g., mean $t_{max}$) represents the arithmetic mean value of the pharmacokinetic value unless otherwise specified.

The term "bioavailability" as used herein means the degree or ratio (%) to which a drug or agent is absorbed or otherwise available to the treatment site in the body. This is calculated by the formula $$\text{Rel. Bioavailability}(\%) = \frac{\text{Dose } SC}{\text{Dose Oral}} \times \frac{AUC_{GLP-1} \text{ Oral}}{AUC_{GLP-1} \text{ } SC} \times 100$$

where "SC" refers to subcutaneous.

The term "biopotency" as used herein means the degree or ratio (%) to which a drug or agent is effective to the treatment site in the body. This is calculated by the formula $$\text{Rel. Biopotency}(\%) = \frac{\text{Dose } SC}{\text{Dose Oral}} \times \frac{AUC_{GIR} \text{ Oral}}{AUC_{GIR} \text{ } SC} \times 100$$

where GIR is glucose infusion rate.

The term "$t_{1/2}$" as used herein means the terminal half-life calculated as $\ln(2)/K_{el}$.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

GLP-1

The GLP-1 compounds of the present invention can be made by methods known in the art, such as solid-phase synthetic chemistry, purification of GLP-1 molecules from natural sources, recombinant DNA technology, or a combination of these methods. For example, methods for preparing GLP-1 peptides are described in U.S. Pat. Nos. 5,118,666; 5,120, 712; 5,512,549; 5,977,071; and 6,191,102, all of which are hereby incorporated by reference.

By custom in the art, the amino terminus of GLP-1(7-37) OH has been assigned number residue 7, and the carboxy-terminus has been assigned number 37. The other amino acids in the polypeptide are numbered consecutively, as shown in SEQ ID NO.: 1. For example, position 12 is phenylalanine and position 22 is glycine.

The two naturally occurring truncated GLP-1 peptides are represented in

SEQ ID NO: 1:
His$^7$-Ala-Glu-Gly$^{10}$-Thr-Phe-Thr-Ser-Asp-Val-Ser-

Ser-Tyr-Leu$^{20}$-Glu-Gly-Gln-Ala-Ala$^{25}$-Lys-Glu-Phe-

Ile-Ala$^{30}$-Trp-Leu-Val-Lys-Gly$^{35}$-Arg-Xaa$^{37}$ wherein Xaa$^{37}$ is Gly, or —NH$_2$.

Preferably, a GLP-1 compound has the amino acid sequence of SEQ ID NO.: 1 or is modified so that from one, two, three, four or five amino acids differ from SEQ ID NO.: 1.

A preferred group of GLP-1 compounds is composed of GLP-1 analogs of

SEQ ID NO.: 2:
His-Xaa$^8$-Xaa$^9$-Gly-Xaa$^{11}$-Phe-Thr-Xaa$^{14}$-Asp-Xaa$^{16}$-

Xaa$^{17}$-Xaa$^{18}$-Xaa$^{19}$-Xaa$^{20}$-Xaa$^{21}$-Xaa$^{22}$-Xaa$^{23}$-Xaa$^{24}$-

Xaa$^{25}$-Xaa$^{26}$-Xaa$^{27}$-Phe-Ile-Xaa$^{30}$-Xaa$^{31}$-Xaa$^{32}$-Xaa$^{33}$-

Xaa$^{34}$-Xaa$^{35}$-Xaa$^{36}$-Xaa$^{37}$-Xaa$^{38}$-Xaa$^{39}$-Xaa$^{40}$-Xaa$^{41}$-

Xaa$^{42}$-Xaa$^{43}$-Xaa$^{44}$-Xaa$^{45}$ wherein:
Xaa$^8$ is Ala, Gly, Ser, Thr, Leu, Ile, Val, Glu, Asp, or Lys;
Xaa$^9$ is Glu, Asp, or Lys;
Xaa$^{11}$ is Thr, Ala, Gly, Ser, Leu, Ile, Val, Glu, Asp, or Lys;
Xaa$^{14}$ is Ser, Ala, Gly, Thr, Leu, Ile, Val, Glu, Asp, or Lys;
Xaa$^{16}$ is Val, Ala, Gly, Ser, Thr, Leu, Ile, Tyr, Glu, Asp, Trp, or Lys;
Xaa$^{17}$ is Ser, Ala, Gly, Thr, Leu, Ile, Val, Glu, Asp, or Lys;
Xaa$^{18}$ is Ser, Ala, Gly, Thr, Leu, Ile, Val, Glu, Asp, Trp, Tyr, or Lys;
Xaa$^{19}$ is Tyr, Phe, Trp, Glu, Asp, Gln, or Lys;
Xaa$^{20}$ is Leu, Ala, Gly, Ser, Thr, Ile, Val, Glu, Asp, Met, Trp, Tyr, or Lys;
Xaa$^{21}$ is Glu, Asp, or Lys;
Xaa$^{22}$ is Gly, Ala, Ser, Thr, Leu, Ile, Val, Glu, Asp, or Lys;
Xaa$^{23}$ is Gln, Asn, Arg, Glu, Asp, or Lys;
Xaa$^{24}$ is Ala, Gly, Ser, Thr, Leu, Ile, Val, Arg, Glu, Asp, or Lys;
Xaa$^{25}$ is Ala, Gly, Ser, Thr, Leu, Ile, Val, Glu, Asp, or Lys;
Xaa$^{26}$ is Lys, Arg, Gln, Glu, Asp, or His;
Xaa$^{27}$ is Leu, Glu, Asp, or Lys;
Xaa$^{30}$ is Ala, Gly, Ser, Thr, Leu, Ile, Val, Glu, Asp, or Lys;
Xaa$^{31}$ is Trp, Phe, Tyr, Glu, Asp, of Lys;
Xaa$^{32}$ is Leu, Gly, Ala, Ser, Thr, Ile, Val, Glu, Asp, or Lys;
Xaa$^{33}$ is Val, Gly, Ala, Ser, Thr, Leu, Ile, Glu, Asp, or Lys;
Xaa$^{34}$ is Asn, Lys, Arg, Glu, Asp, or His;
Xaa$^{35}$ is Gly, Ala, Ser, Thr, Leu, Ile, Val, Glu, Asp, or Lys;
Xaa$^{36}$ is Gly, Arg, Lys, Glu, Asp, or His;
Xaa$^{37}$ is Pro, Gly, Ala, Ser, Thr, Leu, Ile, Val, Glu, Asp, or Lys, or is deleted;
Xaa$^{38}$ is Ser, Arg, Lys, Glu, Asp, or His, or is deleted;
Xaa$^{39}$ is Ser, Arg, Lys, Glu, Asp, or His, or is deleted;
Xaa$^{40}$ is Gly, Asp, Glu, or Lys, or is deleted;
Xaa$^{41}$ is Ala, Phe, Trp, Tyr, Glu, Asp, or Lys, or is deleted;
Xaa$^{42}$ is Ser, Pro, Lys, Glu, or Asp, or is deleted;
Xaa$^{43}$ is Ser, Pro, Glu, Asp, or Lys, or is deleted;
Xaa$^{44}$ is Gly, Pro, Glu, Asp, or Lys, or is deleted; and
Xaa$^{45}$ is Ala, Ser, Val, Glu, Asp, or Lys, Ala-NH$_2$, Ser-NH$_2$, Val-NH$_2$, Glu-NH$_2$, Asp-NH$_2$, or Lys-NH$_2$ or is deleted;
provided that when the amino acid at position 37, 38, 39, 40, 41, 42, 43 or 44 is deleted, then each amino acid downstream of that amino acid is also deleted.

The GLP-1 compound of SEQ ID NO: 2 contain less than six amino acids that differ from the corresponding amino acid in GLP-1 (7-37)OH or Exendin-4. It is more preferred that less than five amino acids differ from the corresponding amino acid in GLP-1 (7-37)OH or Exendin-4. It is even more preferred that less than four amino acids differ from the corresponding amino acid in GLP-1(7-37)OH or Exendin-4.

GLP-1 compounds of the present invention include derivatives of SEQ ID NO.: 2 such as a C$_{1-6}$-ester, or amide, or C$_{1-6}$-alkylamide, or C$_{1-6}$-dialkylamide thereof. WO 99/43706 describes derivatives of GLP-1 compounds of SEQ ID NO.: 2 and is incorporated by reference herein in its entirety. The compounds of SEQ ID NO.: 2 derivatized as described in WO 99/43706 and underivatized are encompassed by the present invention.

Another preferred group of GLP-1 compounds is composed of GLP-1 analogs of

SEQ. ID NO.: 3:
Xaa$^7$-Xaa$^8$-Xaa$^9$-Gly-Xaa$^{11}$-Xaa$^{12}$-Thr-Ser-Asp-Xaa$^{16}$-

Ser-Xaa$^{18}$-Xaa$^{19}$-Leu-Glu-Gly-Xaa$^{23}$-Xaa$^{24}$-Ala-Xaa$^{26}$-

Xaa$^{27}$-Phe-Ile-Xaa$^{30}$-Xaa$^{31}$-Leu-Xaa$^{33}$-Xaa$^{34}$-Xaa$^{35}$-

Xaa$^{36}$-R$^{37}$ wherein:
Xaa$^7$ is: L-histidine D-histidine, desamino-histidine, 2-amino-histidine, β-hydroxy-histidine, homohistidine, α-fluoromethyl-histidine or α-methyl-histidine;
Xaa$^8$ is: Gly, Ala, Val, Leu, Ile, Ser, or Thr;
Xaa$^9$ is: Thr, Ser, Arg, Lys, Trp, Phe, Tyr, Glu, or His;
Xaa$^{11}$ is: Asp, Glu, Arg, Thr, Ala, Lys, or His;
Xaa$^{12}$ is: His, Trp, Phe, or Tyr;
Xaa$^{16}$ is: Leu, Ser, Thr, Trp, His, Phe, Asp, Val, Tyr, Glu, or Ala;
Xaa$^{18}$ is: His, Pro, Asp, Glu, Arg, Ser, Ala, or Lys;
Xaa$^{19}$ is: Gly, Asp, Glu, Gln, Asn, Lys, Arg, or Cys;
Xaa$^{23}$ is: His, Asp, Lys, Glu, Gln, or Arg;
Xaa$^{24}$ is: Glu, Arg, Ala, or Lys;
Xaa$^{26}$ is: Trp, Tyr, Phe, Asp, Lys, Glu, or His;
Xaa$^{27}$ is: Ala, Glu, His, Phe, Tyr, Trp, Arg, or Lys;
Xaa$^{30}$ is: Ala, Glu, Asp, Ser, or His;
Xaa$^{31}$ is: Asp, Glu, Ser, Thr, Arg, Trp, or Lys;
Xaa$^{33}$ is: Asp, Arg, Val, Lys, Ala, Gly, or Glu;
Xaa$^{34}$ is: Glu, Lys, or Asp;
Xaa$^{35}$ is: Thr, Ser, Lys, Arg, Trp, Tyr, Phe, Asp, Gly, Pro, His, or Glu;
Xaa$^{36}$ is: Thr, Ser, Asp, Trp, Tyr, Phe, Arg, Glu, or His;
R$^{37}$ is: Lys, Arg, Thr, Ser, Glu, Asp, Trp, Tyr, Phe, His Gly, Gly-Pro, or is deleted.

Another group of GLP-1 compounds is composed of GLP-1 analogs of

SEQ ID NO: 4:
Xaa$^7$-Xaa$^8$-Glu-Gly-Xaa$^{11}$-Xaa$^{12}$-Thr-Ser-Asp-Xaa$^{16}$-

Ser-Ser-Tyr-Leu-Glu-Xaa$^{22}$-Xaa$^{23}$-Xaa$^{24}$-Xaa$^{25}$-Lys-

Xaa$^{27}$-Phe-Ile-Xaa$^{30}$-Trp-Leu-Xaa$^{33}$-Xaa$^{34}$-Xaa$^{35}$-

Xaa$^{36}$-R$^{37}$ wherein:
Xaa$^7$ is: L-histidine, D-histidine, desamino-histidine, 2-amino-histidine, B-hydroxy-histidine, homohistidine, a-fluoromethylhistidine or a-methylhistidine;
Xaa$^8$ is: Gly, Ala, Val, Leu, Ile, Ser, or Thr;

Xaa¹¹ is: Asp, Glu, Arg, Thr, Ala, Lys, or His;
Xaa¹² is: His, Trp, Phe, or Tyr;
Xaa¹⁶ is: Leu, Seri Thr, Trp, His, Phe, Asp, Val, Glu, or Ala;
Xaa²² is: Gly, Asp, Glu;
Xaa²³ is: His, Asp, Lys, Glu, or Gln;
Xaa²⁴ is: Glu, His, Ala, or Lys;
Xaa²⁴ is: Asp, Lys, Glu, or His;
Xaa²⁷ is: Ala, Glu, His, Phe, Tyr, Trp, Arg, or Lys;
Xaa³⁰ is: Ala, Glu, Asp, Ser, or His;
Xaa³³ is: Asp, Arg, Val, Lys, Ala, Gly, or Glu;
Xaa³⁴ is: Glu, Lys, or Asp;
Xaa³⁵ is: Thr, Ser, Lys, Arg, Trp, Tyr, Phe, Asp, Gly, Pro, His, or Glu;
Xaa³⁶ is: Arg, Glu, or His;
R³⁷ is: Lys, Arg, Thr, Ser, Glu, Asp, Trp, Tyr, Phe, His, Gly, Gly-Pro, or is deleted.

Another group of GLP-1 compounds is composed of GLP-1 analogs of

SEQ ID NO: 5:
Xaa⁷-Xaa⁸-Glu-Gly-Thr-Xaa¹²-Thr-Ser-Asp-Xaa¹⁶-Ser-

Ser-Tyr-Leu-Glu-Xaa²²-Xaa²³-Ala-Ala-Xaa²⁶-Glu-Phe-

Ile-Xaa³⁰-Trp-Leu-Val-Lys-Xaa³⁵-Arg-R³⁷ wherein:
Xaa⁷ is: L-histidine, D-histidine, desamino-histidine, 2-amino-histidine, B-hydroxy-histidine, homohistidine, a-fluoromethyl-histidine, or a-methyl-histidine;
Xaa⁸ is: Gly, Ala, Val, Leu, Ile, Ser, Met, or Thr;
Xaa¹² is: His, Trp, Phe, or Tyr;
Xaa¹⁶ is: Leu, Ser, Thr, Trp, His, Phe, Asp, Val, Glu, or Ala;
Xaa²² is: Gly, Asp, Glu, Gln, Asn, Lys, Arg, or Cys;
Xaa²³ is: His, Asp, Lys, Glu, or Gln;
Xaa²⁶ is: Asp, Lys, Glu, or His;
Xaa³⁰ is: Ala, Glu, Asp, Ser, or His;
Xaa³⁵ is: Thr, Ser, Lys, Arg, Trp, Tyr, Phe, Asp, Gly, Pro, His, or Glu;
R³⁷ is: Lys, Arg, Thr, Ser, Glu, Asp, Tip, Tyr, Phe, His, Gly, Gly-Pro, or is deleted.

Another group of GLP-1 compounds is composed of GLP-1 analogs of

SEQ ID NO: 6:
Xaa⁷-Xaa⁸-Glu-Gly-Thr-Phe-Thr-Ser-Asp-Val-Ser-Ser-

Tyr-Leu-Glu-Xaa²²-Xaa²³-Xaa²⁴-Ala-Lys-Glu-Phe-Ile-

Xaa³⁰-Trp-Leu-Val-Lys-Gly-Arg-R³⁷ wherein
Xaa⁷ is: L-histidine, D-histidine, desamino-histidine, 2-amino-histidine, β-hydroxy-histidine, homohistidine, α-fluoromethyl-histidine, or α-methyl-histidine
Xaa⁸ is: Gly, Ala, Val, Leu, Ile, Ser, or Thr;
Xaa²² is: Gly, Asp, Glu, Gln, Asn, Lys, Arg, or Cys;
Xaa²³ is: His, Asp, Lys, Gln, or Gln;
Xaa²⁴ is: Ala, Glu, Asp, Ser, or His;
Xaa³⁰ is: Ala, Glu, Asp, Ser, or His;
R³⁷ is: Lys, Arg, Thr, Ser, Glu, Asp, Trp, Tyr, Phe, His, Gly, Gly-Pro, or is deleted.

According to one embodiment, GLP-1 compounds of SEQ ID NOS.: 2, 3, 4, 5, and 6 comprise GLP-1 analogs or fragments of GLP-1 analogs wherein the analogs or fragments contain an amino acid other than alanine at position 8 (position 8 analogs). These position 8 analogs may contain one or more additional changes at positions 9, 11, 12, 16, 18, 22, 23, 24, 26, 27, 30, 31, 33, 34, 35, 36, and 37 compared to the corresponding amino acid of native GLP-1 (7-37)OH. These analogs, for example, may have 6 or fewer changes compared to the corresponding amino acids in native GLP-1(7-37)OH or GLP-1(7-36)OH. According to another embodiment, these analogs have 5 or fewer changes compared to the corresponding amino acids in native GLP-1(7-37)OH or GLP-1(7-36) OH or have 4 or fewer changes compared to the corresponding amino acids in native GLP-1 (7-37)OH or GLP-1 (7-36) OH. According to yet another embodiment, these analogs have 3 or fewer changes compared to the corresponding amino acids in native GLP-1 (7-37)OH or GLP-1 (7-36)OH. According to yet another embodiment, these analogs have 2 or fewer changes compared to the corresponding amino acids in native GLP-1(7-37)OH.

According to another embodiment, GLP-1 compounds of SEQ ID NOS: 2, 3, 4, 5, and 6 comprise GLP-1 analogs or fragments of GLP-1 analogs in which glycine at position 22 and preferably alanine at position 8 have been replaced with another amino acid.

When position 22 is aspartic acid, glutamic acid, arginine or lysine, position 8 is may be glycine, valine, leucine, isoleucine, serine, threonine or methionine. When position 22 is a sulfonic acid such as cysteic acid, position 8 may be glycine, valine, leucine, isoleucine, serine; threonine or methionine.

Other GLP-1 compounds include GLP-1 analogs of SEQ ID NO: 5 wherein the analogs have the sequence of GLP-1 (7-37)OH except that the amino acid at position 8 is glycine, valine, leucine, isoleucine, serine, threonine, or methionine and position 30 is glutamic acid, aspartic acid, serine, or histidine.

Other GLP-1 compounds include GLP-1 analogs of SEQ ID NO: 5 wherein the analogs have the sequence of GLP-1 (7-37)OH except that the amino acid at position 8 is glycine, valine, leucine, isoleucine, serine, threonine, or methionine and position 37 is histidine, lysine, arginine, threonine, serine, glutamic acid, aspartic acid, tryptophan, tyrosine, phenylalanine.

Other preferred GLP-1 compounds include GLP-1 analogs of SEQ ID NO: 5 wherein the analogs have the sequence of GLP-1 (7-37)OH, except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 23 is lysine, arginine, glutamic acid, aspartic acid, and histidine and more preferably lysine or glutamic acid.

Other preferred GLP-1 compounds include GLP-1 analogs of SEQ ID NO: 6 wherein the analogs have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamine acid or lysine and position 27 is alanine, lysine, arginine, tryptophan, tyrosine, phenylalanine, or histidine and more preferably alanine.

Other preferred GLP-1 compounds include GLP-1 analogs of SEQ ID NO: 3 wherein the analogs have the sequence of GLP-1 (7-37)OH except that the amino acid at position 8 and one, two, or three amino acids selected from position 9, position 11, position 12, position 16, position 18, position 22, position 23, position 24, position 26, position 27, position 30, position 31, position 33, position 34, position 35, position 36, and position 37, differ from the amino acid at the corresponding position of native GLP-1 (7-37)OH.

Other preferred GLP-1 compounds of SEQ ID No. 3 include: $Val^8$-GLP-1(7-37) OH, $Gly^8$-GLP-1 (7-37)OH, $Glu^{22}$-GLP-1 (7-37)OH, $Asp^{22}$-GLP-1 (7-37)OH, $Arg^{22}$-GLP-1 (7-37)OH, $Lys^{22}$-GLP-1 (7-37)OH, $Cys^{22}$-GLP-1 (7-37)OH, $Val^8$-$Glu^{22}$-GLP-1 (7-37)OH, $Val^8$-$Asp^{22}$-GLP-1 (7-37)OH, $Val^8$-$Arg^{22}$-GLP-1 (7-37)OH, $Val^8$-$Lys^{22}$-GLP-1 (7-37)OH, $Val^8$-$Cys^{22}$-<GP-1 (7-37)OH, $Gly^8$-$Glu^{22}$-GLP-1 (7-37)OH, $Gly^8$-$Asp^{22}$-GLP-1 (7-37)OH, $Gly^8$-$Arg^{22}$-GLP-1(7-37)OH, $Gly^8$-$Lys^{22}$-GLP-1(7-37)OH, $Gly^8$-$Cys^{22}$-GLP-1(7-37)OH, $Glu^{22}$-GLP-1(7-36)OH, $Asp^{22}$-GLP-1(7-36)OH, $Arg^{22}$-GLP-1(7-36)OH, $Lys^{22}$-GLP-1(7-36)OH, $Cys^{22}$-GLP-1(7-36)OH, $Val^8$-$Glu^{22}$-GLP-1(7-36)OH, $Val^8$-$Asp^{22}$-GLP-1(7-36)OH, $Val^8$-Arg-GLP-1(7-36)OH, $Val^8$-$Lys^{22}$-GLP-1(7-36)OH, $Val^8$-$Cys^{22}$-GLP-1(7-36)OH, $Gly^8$-$Glu^{22}$-GLP-1(7-36)OH, $Gly^8$-$Asp^{22}$-GLP-1(7-36)OH, $Gly^8$-$Arg^{22}$-GLP-1(7-36)OH, $Gly^8$-$Lys^{22}$-GLP-1(7-36)OH, $Gly^8$-$Cys^{22}$-GLP-1(7-36)OH, $Lys^{23}$-GLP-1(7-37)OH, $Val^8$-$Lys^{23}$-GLP-1(7-37)OH, $Gly^8$-$Lys^{23}$-GLP-1(7-37)OH, $His^{24}$-GLP-1(7-37)OH, $Val^8$-$His^{24}$-GLP-1(7-37)OH, $Gly^8$-$His^{24}$-GLP-1(7-37)OH, $Lys^{24}$-GLP-1(7-37)OH, $Val^8$-$Lys^{24}$-GLP-1(7-37)OH, $Glu^{30}$-GLP-1(7-37)OH, $Val^8$-$Glu^{30}$-GLP-1(7-37)OH, $Gly^8$-$Glu^{10}$-GLP-1(7-37)OH, $Asp^{30}$-GLP-1(7-37)OH, $Val^8$-$Asp^{30}$-GLP-1(7-37)OH, $Gly^8$-$Asp^{30}$-GLP-1(7-37)OH, $Gln^{30}$-GLP-1(7-37)OH, $Val^8$-$Gln^{30}$-GLP-1(7-37)OH, $Gly^8$-$Gln^{30}$-GLP-1(7-37)OH, $Tyr^{30}$-GLP-1(7-37)OH, $Val^8$-$Tyr^{30}$-GLP-1(7-37)OH, $Gly^8$-$Tyr^{30}$-GLP-1(7-37)OH, $Ser^{30}$-GLP-1(7-37)OH, $Val^8$-$Ser^{30}$-GLP-1(7-37)OH, $Gly^8$-$Ser^{30}$-GLP-1(7-37)OH, $His^{30}$-GLP-1(7-37)OH, $Val^8$-$His^{30}$-GLP-1(7-37)OH, $Gly^8$-$His^{30}$-GLP-1(7-37)OH, $Glu^{34}$-GLP-1(7-37)OH, $Val^8$-$Glu^{34}$-GLP-1(7-37)OH, $Gly^8$-$Glu^{34}$-GLP-1(7-37)OH, $Ala^{34}$-GLP-1(7-37)OH, $Val^8$-$Ala^{34}$-GLP-1(7-37)OH, $Gly^8$-$Ala^{34}$-GLP-1(7-37)OH, $Gly^{34}$-GLP-1(7-37)OH, $Val^8$-$Gly^{34}$-GLP-1(7-37)OH, $Gly^8$-$Gly^{34}$-GLP-1(7-37)OH, $Ala^{35}$-GLP-1(7-37)OH, $Val^8$-$Ala^{35}$-GLP-1(7-37)OH, $Gly^8$-$Ala^{35}$-GLP-1(7-37)OH, $Lys^{35}$-GLP-1(7-37)OH, $Val^8$-$Lys^{35}$-GLP-1(7-37)OH, $Gly^8$-$Lys^{35}$-GLP-1(7-37)OH, $His^{35}$-GLP-1(7-37)OH, $Val^8$-$His^{35}$-GLP-1(7-37)OH, $Gly^8$-$His^{35}$-GLP-1(7-37)OH, $Pro^{35}$-GLP-1(7-37)OH, $Val^8$-$Pro^{35}$-GLP-1(7-37)OH, $Gly^8$-$Pro^{35}$-GLP-1(7-37)OH, $Glu^{35}$-GLP-1(7-37)OH, $Val^8$-$Glu^{35}$-GLP-1(7-37)OH, $Gly^8$-$Glu^{35}$-GLP-1(7-37)OH, $Val^8$-$Ala^{27}$-GLP-1(7-37)OH, $Val^8$-$His^{37}$-GLP-1(7-37)OH, $Val^8$-$Glu^{22}$-$Lys^{23}$-GLP-1(7-37)OH, $Val^8$-$Glu^{22}$-$Glu^{23}$-GLP-1(7-37)OH, $Val^8$-$Glu^{22}$-$Ala^{27}$-GLP-1(7-37)OH, $Val^8$-$Gly^{34}$-$Lys^{35}$-GLP-1(7-37)OH, $Gly^8$-$His^{37}$-GLP-1(7-37)OH, $Val^8$-$Glu^{22}$-$Ala^{27}$-GLP-1(7-37)OH, $Gly^8$-$Glu^{22}$-$Ala^{27}$-GLP-1(7-37)OH, $Val^8$-$Lys^{22}$-$Glu^{23}$-GLP-1(7-37)OH, and $Gly^8$-$Lys^{22}$-$Glu^{23}$-GLP-1(7-37)OH.

Another preferred group of GLP-1 analogs and derivatives for use in the present invention is composed of molecules of

```
SEQ. ID NO.: 7
R₁-X-Glu-Gly¹⁰-Thr-Phe-Thr-Ser-Asp¹⁵-Val-Ser-Ser-
Tyr-Leu²⁰-Y-Gly-Gln-Ala-Ala²⁵-Lys-Z-Phe-Ile-Ala³⁰-
Trp-Leu-Val-Lys-Gly³⁵-Arg-R₂
``` wherein:

$R_1$ is selected from the group consisting of L-histidine, D-histidine, desamino-histidine, 2-amino-histidine, β-hydroxy-histidine, homohistidine, α-fluoromethyl-histidine, and α-methylhistidine;

X is selected from the group consisting of Ala, Gly, Val, Thr, Ile, and alpha-methyl-Ala;

Y is selected from the group consisting of Glu, Gln, Ala, Thr, Ser, and Gly;

Z is selected from the group consisting of Glu, Gln, Ala, Thr, Ser, and Gly; and $R_2$ is Gly-OH.

Another group of GLP-1 compounds for use in the present invention is disclosed in WO 91/11457, and consists essentially of GLP-1 (7-34), GLP-1 (7-35), GLP-1 (7-36), or GLP-1 (7-37), or the amide form thereof, and pharmaceutically-acceptable salts thereof, having at least one modification selected from the group consisting of (a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of, glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form. Because the enzyme, dipeptidyl-peptidase IV (DPP IV), may be responsible for the observed rapid in vivo inactivation of administered GLP-1, [See, e.g. Mentlein, R., et al., Ear. J. Biochem., 214: 829-835

(1993)], GLP-1 analogs and derivatives that are protected from the activity of DPP IV in the context of a fusion protein are preferred, and fusion proteins wherein the GLP-1 compound is Gly$^8$-GLP-1 (7-37)OH, Val-GLP-1 (7-37)OH, α-methyl-Ala$^8$-GLP-1 (7-37)OH, or Gly$^8$-Gln$^{21}$-GLP-1(7-37)OH are more preferred. Another preferred group of GLP-1 compounds for use in the present invention consists of the compounds of

```
SEQ ID NO:8:
R₁-Ala-Glu-Gly¹⁰-Thr-Phe-Thr-Ser-Asp¹⁵-Val-Ser-Ser-
Tyr-Leu²⁰-Glu-Gly-Gln-Ala-Ala²⁵-Xaa-Glu-Phe-Ile-
Ala³⁰-Trp-Leu-Val-Lys-Gly³⁵-Arg-R₃
                      |
                     R²
``` wherein:
$R_1$ is selected from 4-imidazopropionyl, 4-imidazoacetyl, or 4-imidazo-α,α-dimethyl-acetyl;
$R_2$ is selected from $C_6$-$C_{10}$ unbranched acyl, or is absent;
$R_3$ is selected from Gly-OH or $NH_2$; and
Xaa is Lys or Arg. SEQ ID NO. 8 is disclosed in U.S. Pat. No. 5,512,549, which is hereby incorporated herein by reference.

Examples of compounds of SEQ ID NO.: 8 for use in the present invention are those in which Xaa is Arg and $R_2$ is $C_6$-$C_{10}$ unbranched acyl, such as those in which Xaa is Arg, $R_2$ is $C_6$-$C_{10}$ unbranched acyl, and $R_3$ is Gly-OH. Other examples of compounds of SEQ. ID NO: 8 for use in the present invention are those in which Xaa is Arg, $R_2$ is $C_6$-$C_{10}$ unbranched acyl, $R_3$ is Gly-OH, and $R_1$ is 4-imidazopropionyl, such as the compound in which Xaa is Arg, $R_2$ is $C_8$ unbranched acyl, $R_3$ is Gly-OH, and $R_1$ is 4-imidazopropionyl.

Other GLP-1 derivatives are described in U.S. Pat. No. 6,268,343 B1, such as Arg$^{34}$-Lys$^{26}$-(N-ε-(γ-Glu N-α-hexadecanoyl)))-GLP-1(7-37).

GLP-1 compounds comprise GLP-1 analogs wherein the backbone for such analogs or fragments contains an amino acid other than alanine at position 8 position 8 analogs). The backbone may also include L-histidine, D-histidine, or modified forms of histidine such as desamino-histidine, 2-amino-histidine, B1-hydroxy-histidine, homohistidine, a-fluoromethyl-histidine, or a-methyl-histidine at position 7. These position 8 analogs may contain one or more additional changes at positions 12, 16, 18, 19, 20, 22, 25, 27, 30, 33, and 37 compared to the corresponding amino acid of native GLP-1(7-37)OH. These position 8 analogs may contain one or more additional changes at positions 16, 18, 22, 25 and 33 compared to the corresponding amino acid of native GLP-1 (7-37)OH.

In another embodiment, the GLP-1 analog is GLP-1(7-37)OH wherein the amino acid at position 12 is selected from the group consisting of tryptophan or tyrosine. In addition to the substitution at position 12, the amino acid at position 8 may be substituted with glycine, valine, leucine, isoleucine, serine, threonine, or methionine. In addition to the substitutions at position 12 mid 8, the amino acid at position 22 may be substituted with glutamic acid.

In another embodiment, the GLP-1 analog is GLP-1 (7-37)OH wherein the amino acid at position 16 is selected from the group consisting of tryptophan, isoleucine, leucine, phenylalanine, or tyrosine. In addition to the substitution at position 16, the amino acid at position 8 may be substituted with glycine, valine, leucine, isoleucine, serine, threonine, or methionine. In addition to the substitutions at position 16 and 8, the amino acid at position 22 may be substituted with glutamic acid. In addition to the substitutions at positions 16 and 8, the amino acid at position 30 may be substituted with glutamic acid. In addition to the substitutions at positions 16 and 8, the amino acid at position 37 may be substituted with histidine.

In another embodiment, the GLP-1 analog is GLP-1(7-37)OH wherein the amino acid at position 18 is tryptophan, tyrosine, phenylalanine, lysine, leucine, or isoleucine. In addition to the substitution at position 18, the amino acid at position 8 may be substituted with glycine, valine, leucine, isoleucine, serine, threonine, or methionine. In addition to the substitutions at position 18 and 8, the amino acid at position 22 may be substituted with glutamic acid. In addition to the substitutions at positions 18 and 8, the amino acid at position 30 may be substituted with glutamic acid. In addition to the substitutions at positions 18 and 8, the amino acid at position 37 may be substituted with histidine.

In another embodiment, the GLP-1 analog is GLP-1 (7-37)OH wherein the amino acid at position 19 is tryptophan or phenylalanine. In addition to the substitution at position 19, the amino acid at position 8 may be substituted with glycine, valine, leucine, isoleucine, serine, threonine, or methionine. In addition to the substitutions at position 19 and 8, the amino acid at position 22 may be substituted with glutamic acid. In addition to the substitutions at positions 19 and 8, the amino acid at position 30 may be substituted with glutamic acid. In addition to the substitutions at positions 19 and 8, the amino acid at position 37 may be substituted with histidine.

In another embodiment, the GLP-1 analog is GLP-1(7-37)OH wherein the amino acid at position 20 is phenylalanine, tyrosine, or tryptophan. In addition to the substitution at position 20, the amino acid at position 8 may be substituted with glycine, valine, leucine, isoleucine, serine, threonine, or methionine. In addition to the substitutions at position 20 and 8, the amino acid at position 22 may be substituted with glutamic acid. In addition to the substitutions at positions 20 and 8, the amino acid at position 30 may be substituted with glutamic acid. In addition to the substitutions at positions 20 and 8, the amino acid at position 37 may be substituted with histidine.

In another embodiment, the GLP-1 analog is GLP-1 (7-37)OH wherein the amino acid at position 25 is valine, isoleucine, or leucine. In addition to the substitution at position 25, the amino acid at position 8 may be substituted with glycine, valine, leucine, isoleucine, serine, threonine, or methionine. In addition to the substitutions at position 25 and 8, the amino acid at position 22 may be substituted with glutamic acid. In addition to the substitutions at positions 25 and 8, the amino acid at position 30 may be substituted with glutamic acid. In addition to the substitutions at positions 25 and 8, the amino acid at position 37 may be substituted with histidine.

In another embodiment, the GLP-1 analog is GLP-1(7-37)OH wherein the amino acid at position 27 is isoleucine or alanine. In addition to the substitution at position 27, the amino acid at position 8 may be substituted with glycine, valine, leucine, isoleucine, serine, threonine, or methionine. In addition to the substitutions at position 27 and 8, the amino acid at position 22 may be substituted with glutamic acid. In addition to the substitutions at positions 27 and 8, the amino acid at position 30 may be substituted with glutamic acid. In addition to the substitutions at positions 27 and 8, the amino acid at position 37 may be substituted with histidine.

In another embodiment, the GLP-1 analog is GLP-1(7-37)OH wherein the amino acid at position 33 is isoleucine. In addition to the substitution at position 33, the amino acid at position 8 may be substituted with glycine, valine, leucine, isoleucine, serine, threonine, or methionine. In addition to the substitutions at position 33 and 8, the amino acid at position 22 may be substituted with glutamic acid. In addition to the substitutions at positions 33 and 8, the amino acid at position 30 may be substituted with glutamic acid. In addition to the substitutions at positions 33 and 8, the amino acid at position 37 may be substituted with histidine.

The GLP-1 compounds have modifications at one or more of the following positions: 8, 12, 16, 18, 19, 20, 22, 25, 27, 30, 33, and 37. These GLP-1 compounds show increased potency compared with GLP-1 (7-37)OH and comprise the amino acid sequence of

```
SEQ ID NO.: 9:
Xaa⁷-Xaa⁸-Glu-Gly-Thr-Xaa¹²-Thr-Ser-Asp-Xaa¹⁶-Ser-

Xaa¹⁸-Xaa¹⁹-Xaa²⁰-Glu-Xaa²²-Gln-Ala-Xaa²⁵-Lys-Xaa²⁷-

Phe-Ile-Xaa³⁰-Trp-Leu-Xaa³³-Lys-Gly-Arg-Xaa³⁷
``` wherein:
Xaa⁷ is: L-histidine, D-histidine, desamino-histidine, 2-amino-histidine, β-hydroxy-histidine, homohistidine, a-fluoromethyl-histidine, or α-methyl-histidine;
Xaa⁸ is: Ala, Gly, Val, Leu, Ile, Ser, or Thr;
Xaa¹² is: Phe, Trp, or Tyr;
Xaa¹⁶ is: Val, Trp, Ile, Leu, Phe, or Tyr;
Xaa¹⁸ is: Ser, Trp, Tyr, Phe, Lys, Ile, Leu, Val;
Xaa¹⁹ is: Tyr, Trp, or Phe;
Xaa²⁰ is: Leu, Phe, Tyr, or Trp;
Xaa²² is: Sly, Glu, Asp, or Lys;
Xaa²⁵ is: Ala, Val, Ile, or Leu;
Xaa²⁷ is: Glu, Ile, or Ala;
Xaa³⁰ is: Ala or Glu;
Xaa³³ is: Val or Ile; and
Xaa³⁷ is: Gly, His, NH₂, or is absent.

Examples of GLP-1 compounds of SEQ ID NO:9 include GLP-1 (7-37)OH, GLP-1 (7-36)NH₂, Gly⁸-GLP-1 (7-37)OH, Gly⁸-GLP-1 (7-36)NH₂, Val⁸-GLP-1 (7-37)OH, Val⁸-GLP-1 (7-36)NH₂, Leu⁸-GLP-1 (7-37)OH, Leu⁸-GLP-1 (7-36)NH₂, Ile⁸-GLP-1 (7-37)OH, Ile⁸-GLP-1 (7-36)NH₂, Ser⁸-GLP-1 (7-37)OH, Ser⁸-GLP-1 (7-36)NH₂, Thr⁸-GLP-1 (7-37)OH, Thr⁸-GLP-1 (7-36)NH₂, Val⁸-Tyr¹²-GLP-1 (7-37)OH, Val⁸-Tyr¹²-GLP-1 (7-36)NH₂, Val⁸-Tyr¹⁶-GLP-1 (7-37)OH, Val⁸-Tyr¹⁶-GLP-1 (7-36)NH₂, Val⁸-Tyr¹⁶-Glu²²-GLP-1 (7-37)OH, Val⁸-Trp¹⁶-Glu²²-GLP-1 (7-37)OH, Val⁸-Leu¹⁶-Glu²²-GLP-1 (7-37)OH, Val⁸-Ile¹⁶-Glu²²-GLP-1 (7-37)OH, Val⁸-Phe¹⁶-Glu²²-GLP-1 (7-37)OH, Val⁸-Trp¹⁸-Glu²²-GLP-1 (7-37)OH, Val⁸-Tyr¹⁸-Glu²²-GLP-1 (7-37)OH, Val⁸-Phe¹⁸-Glu²²-GLP-1 (7-37)OH, and Val⁸-Ile¹⁸-Glu²²-GLP-1 (7-37)OH, Glu²²-GLP-1(7-36)NH₂, Asp²²-GLP-1(7-37)OH, Asp²²-GLP-1(7-36)NH₂, Lys²²-GLP-1(7-37OH), Lys²²-GLP-1 (7-36NH₂), Val⁸-Ala²⁷-GLP-1(7-37)OH, Val⁸-Glu²²-Ala²⁷-GLP-1(7-37)OH, Val⁸-Glu³⁰-GLP-1(7-37)OH, Val⁸-Glu³⁰-GLP-1 (7-36)NH₂, Gly⁸-Glu³⁰-GLP-1(7-37)OH, Gly⁸-Glu³⁰-GLP-1(7-36)NH₂, Leu⁸-Glu³⁰-GLP-1(7-37)OH, Leu⁸-Glu³⁰-GLP-1 (7-36)NH₂, Ile⁸-Glu³⁰-GLP-1(7-37)OH, Ile⁸-Glu³⁰-GLP-1(7-36)NH₂, Ser⁸-Glu³⁰-GLP-1(7-37)OH, Ser⁸-Glu³⁰-GLP-1(7-36)NH₂, Thr⁸-Glu³⁰-GLP-1(7-37)OH, Thr⁸-Glu³⁰-GLP-1(7-36)NH₂, Val⁸-His³⁷-GLP-1(7-37)OH, Val⁸-His³⁷-GLP-1(7-36)NH₂, Gly⁸-His³⁷-GLP-1 (7-37)OH, Gly⁸-His³⁷-GLP-1(7-36)NH₂, Leu⁸-His³⁷-GLP-1(7-37)OH, Leu⁸-His³⁷-GLP-1(7-36)NH₂, Ile⁸-His³⁷-GLP-1(7-37)OH, Ile⁸-His³⁷-GLP-1(7-36)NH₂, Ser⁸-His³⁷-GLP-1 (7-37)OH, Ser⁸-His³⁷-GLP-1(7-36)NH₂, Thr⁸-His³⁷-GLP-1 (7-37)OH, Thr⁸-His³⁷-GLP-1(7-36)NH₂.

Examples of GLP-1 compounds of SEQ ID NO.: 9 having multiple substitutions include GLP-1(7-37)OH wherein position 8 is valine or glycine, position 22 is glutamic acid, position 16 is tyrosine, leucine or tryptophan, position 18 is tyrosine, tryptophan, or isoleucine, position 25 is valine and position 33 is isoleucine. Other such GLP-1 compounds include the following; Val⁸-Tyr¹⁶-GLP-1(7-37)OH, Val⁸-Tyr¹²-Glu²²-GLP-1 (7-37)OH, Val⁸-Tyr¹⁶-Phe¹⁹-GLP-1 (7-37)OH, Val⁸-Tyr¹⁶-Glu²²-GLP-1 (7-37)OH, Val⁸-Trp¹⁶-Glu²²-GLP-1 (7-37)OH, Val⁸-Leu¹⁶-Glu²²-GLP-1(7-37) OH, Val⁸-Ile¹⁶-Glu²²-GLP-1 (7-37)OH, Val⁸-Phe¹⁶-Glu²²-GLP-1(7-37)OH, Val⁸-Trp¹¹-Glu²²-GLP-1(7-37)OH, Val⁸-Tyr¹⁸-Glu²²-GLP-1(7-37)OH, Val⁸-Phe¹⁸-Glu²²-GLP-1(7-37)OH, and Val⁸-Ile¹⁸-Glu²²-GLP-1 (7-37)OH.

The GLP-1 compounds of the present invention also encompass Exendin compounds. Exendin-3 and Exendin-4 are biologically active peptides first isolated from Helodermatidae lizard venoms and have been shown to bind the GLP-1 receptor and stimulate cAMP-dependent H+ production in mammalian parietal cells. Exendin-3 and Exendin-4 are both 39 amino acid peptides which are approximately 53% homologous to GLP-1. They act as potent agonists of GLP-1 activity. Notably, an N-terminally truncated derivative of Exendin, known as Exendin (9-39 amino acids), is an inhibitor of Exendin-3, Exendin-4 and GLP-1.

An Exendin compound typically comprises a polypeptide having the amino acid sequence of Exendin-3, Exendin-4, or an analog or fragment thereof. Exendin-3 and Exendin-4 are disclosed in U.S. Pat. No. 5,424,286, which is hereby incorporated by reference.

Exendin-3 has the amino acid sequence of

```
SEQ ID NO.: 10:
His⁷-Ser-Asp-Gly¹⁰-Thr-Phe-Thr-Ser-Asp¹⁵-Leu-Ser-

Lys-Gln-Met²⁰-Glu-Glu-Glu-Ala-Val²⁵-Arg-Leu-Phe-

Ile-Glu³⁰-Trp-Leu-Lys-Asn-Gly³⁵-Gly-Pro-Ser-Ser-

Gly⁴⁰-Ala-Pro-Pro-Pro-Ser⁴⁵-NH₂
```

Exendin-4 has the amino acid sequence of

```
SEQ ID NO.: 11:
His⁷-Gly-Glu-Gly¹⁰-Thr-Phe-Thr-Ser-Asp¹⁵-Leu-Ser-

Lys-Gln-Met²⁰-Glu-Glu-Glu-Ala-Val²⁵-Arg-Leu-Phe-

Ile-Glu³⁰-Trp-Leu-Lys-Asn-Gly³⁵-Gly-Pro-Ser-Ser-

Gly⁴⁰-Ala-Pro-Pro-Pro-Ser⁴⁵-NH₂.
```

GLP-1 compounds also include Exendin fragments which are polypeptides obtained after truncation of one or more amino acids from the N-terminus and/or C-terminus of Exendin or an Exendin analog. Furthermore, GLP-1 compounds include Exendin polypeptides in which one or more amino acids have been added to the N terminus and/or C-terminus of Exendin or fragments thereof. Exendin compounds of this type have up to about forty-five amino acids.

GLP-1 compounds also include "Exendin analogs". An Exendin analog has sufficient homology to Exendin-4, Exendin-3, or a fragment thereof such that the analog has insulinotropic activity. The activity of Exendin fragments and/or analogs can be assessed using in vitro assays.

An Exendin analog has the amino acid sequence of Exendin-4 or a fragment thereof, may be modified so that from one, two, three, four or five amino acids differ from the amino acid in corresponding position of Exendin-4 or the fragment of Exendin-4. In the nomenclature used herein to designate Exendin compounds, the substituting amino acid and its position is indicated prior to the parent structure. For example, $Val^8$-Exendin-4 designates an Exendin compound in which the glycine normally found at position 8 of Exendin-4 has been replaced with valine.

Another group of GLP-1 compounds is composed of GLP-1/Exendin-4 analogs of

```
SEQ ID NO.: 12:
Xaa7-Xaa8-Glu-Gly-Thr-Phe-Thr-Ser-Asp-Xaa16-Ser-

Xaa18-Xaa19-Xaa20-Glu-Xaa22-Xaa23-Ala-Xaa25-Xaa26-

Xaa27-Phe-Ile-Xaa30-Trp-Leu-Xaa33-Xaa34-Gly-Xaa36-

R37
``` wherein:
$Xaa^7$ is: L-histidine, D-histidine, desamino-histidine, 2-amino-histidine, 13-hydroxy-histidine, homohistidine, α-fluoromethyl-histidine or α-methyl-histidine;
$Xaa^8$ is: Gly, Ala, or Val;
$Xaa^{16}$ is: Leu or Val;
$Xaa^{18}$ is Lys or Ser;
$Xaa^{19}$ is: Gln or Tyr;
$Xaa^{20}$ is: Met or Leu;
$Xaa^{22}$ is: Glu or Gln
$Xaa^{23}$ is: Glu or Gln;
$Xaa^{25}$ is: Val or Ala;
$Xaa^{26}$ is: Arg or Lys;
$Xaa^{27}$ is: Leu or Glu;
$Xaa^{30}$ is: Glu or Ala;
$Xaa^{33}$ is: Val or Lys;
$Xaa^{34}$ is: Asn or Lys;
$Xaa^{36}$ is: Gly or Arg; and
$R^{37}$ is: Gly, Pro, Pro-Ser-Ser-Gly-Ala-Pro-Pro-Pro-Ser, or is absent.

Further Exendin-analogs that are useful for the present invention are described in PCT patent publications WO 99/25728 (Beeley, et al.); WO 99/25727 (Beeley, et al.); We 98/05351 (Young, et al.); WO 99/40788 (Young, et al.); WO 99/07404 (Beeley, et al.); and WO 99/43708 (Knudsen, et al.), all of which are hereby incorporated by reference.

Another preferred group of GLP-1 compounds has the amino acid sequence of

```
SEQ ID NO.: 13:
Xaa7-Xaa8-Glu-Gly-Thr-Xaa12-Thr-Ser-Asp-Xaa16-Ser-

Xaa18-Xaa19-Xaa20-Glu-Xaa22-Gln-Ala-Xaa25-Lys-

Xaa27-Phe-Ile-Xaa30-Trp-Leu-Xaa33-Xaa34-Gly-Xaa36-

Xaa37-Xaa38-Xaa39-Xaa40-Xaa41-Xaa42-Xaa43-Xaa44-

Xaa45-Xaa46-Xaa47
``` wherein:
$Xaa^7$ is: L-histidine, D-histidine, desamino-histidine, 2-amino-histidine, -hydroxy-histidine, homohistidine, α-fluoromethyl-histidine, or α-methyl-histidine;
$Xaa^8$ is: Ala, Gly, Val, Leu, Ile, Ser, or Thr;
$Xaa^{12}$ is: Phe, Trp, or Tyr;
$Xaa^{16}$ is: Val, Trp, Ile, Leu, Phe, or Tyr;
$Xaa^{18}$ is: Ser, Trp, Tyr, Phe, Lys, Ile, Leu, Val;
$Xaa^{19}$ is: Tyr, Trp, or Phe;
$Xaa^{20}$ is: Leu, Phe, Tyr, or Trp;
$Xaa^{22}$ is: Gly, Glu, Asp, or Lys;
$Xaa^{25}$ is: Ala, Val, Ile, or Leu;
$Xaa^{27}$ is: Glu, Ile, or Ala;
$Xaa^{30}$ is: Ala or Glu;
$Xaa^{33}$ is: Val or Ile;
$Xaa^{34}$ is: Lys, Asp, Arg, or Glu;
$Xaa^{36}$ is: Gly, Pro, or Arg;
$Xaa^{37}$ is: Gly, Pro, or Ser;
$Xaa^{38}$ is: Ser, Pro, or His;
$Xaa^{39}$ is: Ser, Arg, Thr, Trp, or Lys;
$Xaa^{40}$ is: Ser or Gly;
$Xaa^{41}$ is: Ala, Asp, Arg, Glu, Lys, or Gly;
$Xaa^{42}$ is: Pro, Ala, $NH_2$, or is absent;
$Xaa^{43}$ is: Pro, Ala, $NH_2$, or is absent;
$Xaa^{44}$ is: Pro, Ala, Arg, Lys, His, $NH_2$, or is absent;
$Xaa^{45}$ is: Ser, His, Pro, Lys, Arg, $NH_2$ or is absent;
$Xaa^{46}$ is: His, Ser, Arg, Lys, $NH_2$ or is absent; and
$Xaa^{47}$ is: His, Ser, Arg, Lys, $NH_2$ or is absent; provided that if $Xaa^{42}$, $Xaa^{43}$ $Xaa^{44}$, $Xaa^{45}$, $Xaa^{46}$, or $Xaa^{47}$ is absent each amino acid downstream is absent and further provided that the GLP-1 peptide does not have the following C-terminal amino acid extension beginning at $Xaa^{36}$: Gly-Pro-Ser-Ser-Gly-Ala-Pro-Pro-Pro-Ser-$NH_2$.

Another group of GLP-1 compounds has the amino acid sequence of

```
SEQ ID NO: 14
Xaa7-Xaa8-Glu-Gly-Thr-Phe-Thr-Ser-Asp-Xaa16-Ser-

Ser-Tyr-Lys-Glu-Xaa22-Gln-Ala-Xaa25-Lys-Glu-Phe-

Ile-Ala-Trp-Leu-Xaa33-Xaa34-Gly-Xaa36-Xaa37-Xaa38-

Xaa39-Xaa40-Xaa41-Xaa42-Xaa43-Xaa44-Xaa45-Xaa46-

Xaa47
``` wherein:
$Xaa^7$ is: L-histidine, D-histidine, desamino-histidine, 2-amino-histidine, B-hydroxy-histidine, homohistidine, a-fluoromethyl-histidine, or α-methyl-histidine
$Xaa^8$ is: Gly, Val, Leu, Ile, Ser, or Thr;
$Xaa^{16}$ is: Val, Trp, Ile, Leu, Phe, or Tyr;
$Xaa^{22}$ is: Gly, Glu, Asp, or Lys;
$Xaa^{25}$ is: Ala, Val, Ile, or Leu;
$Xaa^{33}$ is: Val or Ile;
$Xaa^{34}$ is: Lys, Asp, Arg, or Glu;
$Xaa^{36}$ is: Gly, Pro, or Arg;
$Xaa^{37}$ is: Gly, Pro, or Ser;
$Xaa^{38}$ is: Ser, Pro, or His;
$Xaa^{39}$ is: Ser, Arg, Thr, Trp, or Lys;
$Xaa^{40}$ is: Ser or Gly;
$Xaa^{41}$ is: Ala, Asp, Arg, Glu, Lys, or Gly;

Xaa$^{42}$ is: Pro or Ala;
Xaa$^{43}$ is: Pro or Ala;
Xaa$^{44}$ is: Pro, Ala, Arg, Lys, His, NH$_2$ or is absent;
Xaa$^{45}$ is: Ser, His, Pro, Lys, Arg, NH$_2$ or is absent
Xaa$^{46}$ is: His, Ser, Arg, Lys, NH$_2$ or is absent; and
Xaa$^{47}$ is: His, Ser, Arg, Lys, NH$_2$ or is absent;
provided that if Xaa$^{44}$, Xaa$^{45}$, Xaa$^{46}$, or Xaa$^{47}$ is absent each amino acid downstream is absent and further provided that the GLP-1 peptide does not have the following C-terminal amino acid extension beginning at Xaa$^{36}$: Gly-Pro-Ser-Ser-Gly-Ala-Pro-Pro-Pro-Ser-NH$_2$.

Other embodiments of SEQ. ID NOS.: 13 and 14 include GLP-1 compounds that have valine or glycine at position 8 and glutamic acid at position 22.

Other active compounds are suitable for use in formulations of the present invention. These include the agents disclosed in U.S. Pat. Nos. 6,660,716, 6,620,910, 6,608,038, 6,593,295, 6,589,549, 6,586,438, 6,583,111, 6,579,851, 6,576,653, 6,573,291, 6,569,832, 6,566,490, RE38112, 6,555,521, 6,555,519, 6,551,578, 6,548,529, 6,531,124, 6,528,486, 6,518,241, 6,515,117, 6,514,500, 6,500,804, 6,500,645, 6,489,295, 6,485,707, 6,348,447, 6,316,224, 6,303,661, 6,290,987, 6,287,806, 6,284,727, 6,284,725, 6,277,819, 6,271,241, 6,268,343, RE37302, 6,258,377, 6,214,547, 6,201,072, 6,191,102, 6,184,201, 6,180,131, 6,171,823, 6,162,907, 6,133,235, 6,117,949, 6,110,703, 6,087,129, 6,077,949, 6,051,689, 6,048,724, 6,037,145, 6,031,004, 6,017,545, 6,006,753, 6,004,573, 5,994,500, 5,994,127, 5,990,077, 5,985,627, 5,981,488, 5,977,071, 5,958,909, 5,932,547, 5,925,549, 5,912,229, 5,846,937; 5,846,774, 5,846,747, 5,834,428, 5,795,746, 5,789,379, 5,705,483, 5,670,360, 5,639,642, 5,631,224, 5,614,492, 5,574,008, 5,552,520, 5,545,618, 5,512,549, 5,424,286, and 5,118,666. Other agents suitable for use in formulations of the present invention are disclosed in U.S. Published Application Nos. 20030232754, 20030228652, 20030225091, 20030224983, 20030224477, 20030221201, 20030220274, 20030220251, 20030220243, 20030216294, 20030216292, 20030212063, 20030211167, 20030207802, 20030204063, 20030203913, 20030199672, 20030199563, 20030199451, 20030198970 A1, 20030195361, 20030195157, 20030186858, 20030186436, 20030180371, 20030175239, 20030171411, 20030167477, 20030162703, 20030158232, 20030158101, 20030153509, 20030144471, 20030130306, 20030125334, 20030124669, 20030119736, 20030119734, 20030118610, 20030114681, 20030114390, 20030113300, 20030109449, 20030108568, 20030108567, 20030105106, 20030105005, 20030100563, 20030096846, 20030092736, 20030092697, 20030091507, 20030087935, 20030087843, 20030083259, 20030082671, 20030073728, 20030073626, 20030072822 20030069275, 20030069182, 20030064935, 20030060412, 20030050237, 20030045464, 20030041602, 20030040516, 20030040469, 20030027996, 20030022823, 20030022816, 20030008905, 20030004162, 20020198158, 20020187926, 20020183369, 20020183367, 20020177602, 20020165342, 20020165148, 20020155597, 20020155100, 20020151065 20020147131, 20020146779, 20020146405, 20020141979, 20020065239, 20020061901, 20020061838, 20020055460, 20020052392, 20020052326, 20020049153, 20020045582, 20020044976, 20020028826, 20020019411, 20020013268, 20020010129, 20010047084 20010046956, 20010021767, 20010016643, 20010014666, 20010012829, 20010011071, 20010006943, and 20010002394. Other agents suitable for use in formulations of the present invention are disclosed in International Published-Application Nos. 2003102187, 2003101988, 2003100026 2003100022, 2003099991, 2003099853, 2003099852, 2003099848, 2003099847, 2003094845, 2003082841 2003082817, 2003090723, 2003087139, 2003086444, 2003084563, 2003080157, 2003080070, 2003080033, 2003078462, 2003077949, 2003074558, 2003074087, 2003072195, 2003058203, 2003057200, 2003043985, 2003043624, 2003040309, 2003040114, 2003035099, 2003033671, 2003032923, 2003028730, 2003028626, 2003027113, 2003027112, 2003026635, 2003020737, 2003020201, 2003018516, 2003016349, 2003011892, 2003010186, 2003002136, 2003000666, 2003000663, 2003000181, 2003000180, 2002100390 2002098348, 2002096358, 2002096357, 2002085406, 0240537, 0240448, 0247716, 0247715, 0246227, 0243767, 0232395, 0198331, 0187322, 0157084, 0155213, 0154694, 0132158, 0037098, 0016797, 0015224, 0012116, 9947160, 9946283, 9930731, 9929336, 9843658, 9832867, 9820895, 9819698, 9808873, 9808871, 9808531, 9801535, 9739031, 9729180, 9632414, 9620005, 9606628, 9517510, 9504752, 9325579, 9318785, 9210576, and 8706941. Each of the above listed U.S. patents, U.S. Published applications, and Published International applications are herein incorporated by reference.

Delivery Agents

The delivery agents of the present invention can be made by methods known in the art such as those as described in WO 90/36480; WO 96/30036; U.S. Pat. No. 5,643,957; U.S. Pat. No. 6,242,495; all of which are herein incorporated by reference.

The delivery agents of the present invention include those disclosed in WO 96/21464, WO 96/30036, WO 00/06534, WO 98/34632, WO 00/07979, WO 01/44199, WO 1/32596, WO 02/18969, WO 03/045306, and WO 03/072195. Each of these prior applications are incorporated by reference.

Many of the delivery agents of the present invention can be readily prepared from amino acids including, but not limited to, aminocaprylic acid, butyrylhydroxaminic acid, aminophenylbutyric acid, aminophenylhexanoic acid, aminophenylpropionic acid, aminosalicylic acid, aminophenylsuccinic acid, aminononanic acid, aminonicotinic acid, aminovalenic acid, aminophenylacetic acid, aminocaproic acid, aminoundecanoic acid, aminoheptanoic acid, aminohydroxybenzoic acid, and aminodecanoic acid.

For example, these delivery agents may be prepared by reacting the single acid with the appropriate agent which reacts with free amino moiety present in the amino acids to form amides. Protecting groups may be used to avoid unwanted side reactions as would be known to those skilled in the alt.

The delivery agent compounds may be in the form of the free base or salts thereof. Suitable salts include, but are not limited to, organic and inorganic salts, for example sodium, ammonium, acetate salt, citrate salt, halide (preferably hydrochloride), hydroxide, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, citrate and mesylate salts. The salts may also be solvates, including ethanol solvates, and hydrates.

Salts of the delivery agent compounds of the present invention may be prepared by methods known in the art. For example, citrate salts and mesylate salts may be prepared in ethanol, toluene and citric acid.

The delivery agents may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase.

When anion exchange chromatography is performed, preferably a subsequent 0-500 mM sodium chloride gradient is employed.

According to one embodiment, the delivery agents disclosed in International Published Application No. 2003/045306 are excluded as possible delivery agents of the present invention. In one embodiment, compound 1 from International Published Application No. 2003/045306 is excluded. In alternative embodiments, compound 1 and salts of compound 1 are excluded.

In another embodiment, the delivery agents disclosed in International Published Application No. 2002/100338 are excluded. In one embodiment, compound A from International Published Application No. 2002/100338 are excluded. In alternative embodiments, compound A and salts of compound A is excluded. In alternative embodiments, compounds 1-11 of International Published Application No. 2002/100338 are excluded. In alternative embodiments, compounds 1-11 and salts of compounds 1-11 are excluded.

The delivery agent may contain a polymer conjugated to it such as described in WO 03/045306. For example, the delivery agent and polymer may be conjugated by a linkage group selected from the group consisting of —NHC(O)NH—, —C(O)NH—, —NHC(O), —OOC—, —COO—, —NHC(O)O—, —OC(O)NH—, —CH2NH—NHCH2-, —CH2NHC(O)O—, —OC(O)NHCH2—, —CH2NHCOCH2O—, —OCH2C(O)NHCH2-, —NHC(O)CH20-, —OCH2C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals.

Preferred polymers include, but are not limited to, polyethylene; polyacrylates; polymethacrylates; poly(oxyethylene); poly propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Delivery agents of the present invention are described in U.S. Pat. Nos. 6,663,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 5,541,155, 5,693,338, 5,976,569, 5,643,957, 5,955,503, 6,100,298, 5,650,386, 5,866,536, 5,965,121, 5,989,539, 6,001,347, 6,071,510, and 5,820,881. Delivery agents of the present invention are also described in U.S. Published Application Nos. 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, 20010003001. Delivery agents of the present invention are also described in International Published Application Nos. 2003/057650, 2003/057170, 2003/045331, 2003/045306, 2003/026582, 2002/100338, 2002/070438, 2002/069937, 02/20466, 02/19969, 02/16309, 02/15959, 02/02509, 01/92206, 01/70219, 01/51454, 01/44199, 01/34114, 01/32596, 01/32130, 00/07979, 00/59863, 00/50386, 00/47188, 00/40203, 96/30036. Each of the above listed U.S. patents, U.S. Published applications, and Published International applications are herein incorporated by reference.

Administration Composition

The administration compositions of the present invention comprises one or more delivery agent compounds of the present invention, and GLP-1. In one embodiment, one or more of the delivery agent compounds, or salts of these compounds, or poly amino acids or peptides of which these compounds or salts form one or more of the units thereof, may be used as a delivery agent by mixing with the GLP-1 compound prior to administration to form an administration composition.

The administration compositions are preferably in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration composition may also be in the form of a liquid. The solution medium may be water, 25% aqueous propylene glycol, and/or a phosphate buffer. Other dosing vehicles include polyethylene glycol. Dosing solutions may be prepared by mixing a solution of GLP-1 with a solution of the active agent, just prior to administration. Alternately, a solution of the delivery agent compound (or GLP-1) may be mixed with the solid form of the GLP-1 active agent (or delivery agent compound). The delivery agent compound and the GLP-1 may also be mixed as dry powders. The delivery agent compound and GLP-1 can also be admixed during the manufacturing process.

The administration composition of the present invention may optionally encompass a pharmaceutically acceptable buffer. Examples of pharmaceutically acceptable buffers include phosphate buffers such as dibasic sodium phosphate, TRIS, glycylglycine, maleate, sodium acetate, sodium citrate, sodium tartrate, or an amino acid such as glycine, histidine, lysine or arginine. Other pharmaceutically acceptable buffers are known in the art. Preferably, the buffer is selected from the group consisting of phosphate, TRIS, maleate, and glycine. Even more preferably the buffer is TRIS.

Preferably, the TRIS concentration is between about 1 mM and 100 mM. Even more preferably, the concentration is between about 10 mM and about 50 mM, most preferably the buffer is about 20 mM.

The pH of the administration composition may be adjusted to provide stability and to be acceptable for oral administration. The pH may be adjusted to between about 7.0 and about 9.0. More particularly, the pH may be adjusted between about 7.4 and 8.4, or between 7.8 and 8.4, or between about 7.8 and 8.1.

The various oral formulations of the present invention may optionally encompass a suspending agent. Some delivery agents require a suspending agent due to their solubility characteristics. An example of a suspending agent is hydroxypropylmethylcellulose. Preferably, the final concentration of hydroxypropylmethylcellulose is between about 2% and about 10% (weight/volume). Even more preferably, the concentration is between about 2% and about 5% (w/v). Most preferably the concentration is about 3.9% (w/v). The administration composition of the present invention may optionally comprise a cosolvent. Some delivery agents require cosolvents due to their solubility characteristics.

Examples of cosolvents include ethanol, N-methylpyrrolidone, N,N-dimethylacetamide, N,N-dimethylformamide, glycofurol, ethoxydiol, propylene glycol, polyethylene glycol 300 and polyvinylpyrrolidone. Preferably, the final concentration of the cosolvents is between about 5% and about 30% (volume/volume). Even more preferably, the concentration is between about 10% and about 25% (v/v). Most preferably the concentration is about 20% (v/v).

The administration composition may optionally contain additives such as phosphate buffer salts, citric acid, glycols, or other dispersing agents. Stabilizing additives may be incorporated into the solution, preferably at a concentration ranging between about 0.1 and 20% (w/v).

The administration composition of the present invention may optionally comprise a preservative. Preservative refers to a compound that is added to the formulation to act as an antimicrobial agent. Among preservatives known in the art as being effective and acceptable in parenteral formulations are phenolic preservatives, alkylparabens, benzyl alcohol, chlorobutanol, resorcinol, and other similar preservatives, and various mixtures thereof. Examples of phenolic derivatives include cresols and phenol or a mixture of cresols and phenol. Examples of cresols include meta-cresol, ortho-cresol, para-cresol, chlorocresol, or mixtures thereof. Alkylparaben refers to a C1 to C4 alkylparaben, or mixtures thereof. Examples of alkylparabens include methylparaben, ethylparaben, propylparaben, or butylparaben. The concentrations must be sufficient to maintain preservative effectiveness by retarding microbial growth. Preferably, the preservative is a phenol derivative. More preferably the preservative is a cresol. Even more preferably the preservative is meta-cresol.

A preferred concentration of a preservative in the final mixture is about 1.0 mg/mL to about 20.0 mg/mL. More preferred ranges of concentration of preservative in the final mixture are about 2.0 mg/mL to about 8.0 mg/mL, about 2.5 mg/mL to about 4.5 mg/mL and about 2.0 mg/mL to about 4.0 mg/mL. A most preferred concentration of preservative in the final mixture is about 3.0 mg/mL.

The administration composition of the present invention may optionally comprise an isotonicity agent. Isotonicity agents refer to compounds that are tolerated physiologically and impart a suitable tonicity to the formulation to prevent the net flow of water across cell membranes. Examples of such compounds include glycerin, salts, e.g., NaCl, and sugars, e.g., dextrose, mannitol, and sucrose. These compounds are commonly used for such purposes at known concentrations. One or more isotonicity agents may be added to adjust the ionic strength or tonicity. The preferred isotonicity agent is NaCl. The concentration of the NaCl is preferably between about 10 mM and 200 mM, more preferred is between about 50 mM and 150 mM, and most preferred is about 100 mM.

The administration composition of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

Amounts of delivery agents and GLP-1 used in formulations of the present invention will vary according to the severity of the subjects' indication, and the form of GLP-1 and active agent administered. Appropriate amounts for an individual subject can be determined by routine experimentation, in view of the subjects' pharmacokinetic properties, such as insulin levels or glucagon levels in the blood.

Typical amounts of delivery agents and GLP-1 used in testing with male Sprague-Dawly rats range from 0 to 3000 µg/kg of GLP-1, and 0 to 200 µg/kg of delivery agent.

However, because the compositions of the invention may deliver GLP-1 more efficiently than compositions containing GLP-1 alone, lower amounts of GLP-1 than those used in prior dosage unit forms or delivery systems can be administered to the subject, while still achieving the same blood levels and therapeutic effects.

Administration compositions may further include additives. For example administration compositions may include nicotinamide, as disclosed in U.S. Pat. Nos. 6,573,237 and 6,440,930 and U.S. Published Application Nos. U.S. 2003/0221201 and US2003/0069182.

Methods of Treatment

The formulations comprising a GLP-1 compound and a delivery agent can be used to treat a wide variety of diseases and conditions. The GLP-1 compounds primarily exert their biological effects by acting at a GLP-1 receptor. Subjects with diseases and/or conditions that respond favorably to GLP-1 receptor stimulation or to the administration of GLP-1 compounds can therefore be treated with the oral formulations of the present invention.

These subjects are said to "be in need of treatment with GLP-1 compounds" or "in need of GLP-1 receptor stimulation". Included are subjects with non-insulin dependent diabetes, insulin dependent diabetes, stroke (see WO 00/16797), myocardial infarction (see WO 98/08531), obesity (see WO98/19698), catabolic changes after surgery (see U.S. Pat. No. 6,006,753), functional dyspepsia and irritable bowel syndrome (see WO 99/64060). Also included are subjects requiring prophylactic treatment with a GLP-1 compound, e.g., subjects at risk for developing non-insulin dependent diabetes (see WO 00/07617). Subjects with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

Another embodiment of the present invention is a method for the treatment or prevention of a disease or for achieving a desired physiological effect, such in an animal by administering the composition of the present invention. Preferably, an effective amount of the composition for the treatment or prevention of the desired disease or for achieving the desired physiological effect is administered. Specific indications can be found in the Physicians' Desk Reference (54th Ed., 2000, Medical Economics Company, Inc., Montvale, N.J.), which is herein incorporated by reference.

For example, one embodiment of the present invention is a method for treating a patient suffering from or susceptible to diabetes, particularly non-insulin dependent diabetes mellitus (NIDDM) by administering GLP-1 and at least one of the delivery agent compounds of the present invention. Another embodiment of the present invention is a method for treating a subject for obesity by administering GLP-1 and at least one of the delivery agent compounds of the present invention.

Embodiments of the present invention also relate to the prophylactic treatment of subjects who are at risk for non-insulin dependent diabetes. Individuals at risk for non-insulin dependent diabetes are known to those or ordinary skill in the art, and include subjects with impaired glucose tolerance, impaired fasting glucose, overweight subjects, subjects with a partial panreatectomy, subjects having one or more parents with non-insulin dependent diabetes, subjects who have had gestational diabetes, and subjects who, have had acute or chronic pancreatitis.

Embodiments of the present invention further relate to the prophylactic treatment of subjects who are at risk for obesity. Individuals at risk for obesity are known to those or ordinary skill in the art, and include subjects who are already overweight, subjects who have parents or family members who are overweight, subjects who have undergone lifestyle changes such that they are now prone to weight gain (e.g. quitting smoking, the cessation of chronic alcohol or drug use), or subjects who have become incapacitated and/or unable to maintain previous levels of activity.

Following administration, the active agent present in the composition or dosage unit form is taken up into the circulation. The bioavailability of the agent can be readily assessed by measuring a known pharmacological activity in blood, e.g. an increase in insulin caused by the GLP-1 or GLP-1 analog. Alternately, the circulating levels of the GLP-1 or GLP-1 analog itself can be measured directly.

The following non-limiting examples are provided to illustrate the invention. Modifications and variations of the methods and compounds disclosed herein will be apparent to those of ordinary skill in the art, and are intended to be within the scope of the invention.

EXAMPLES

Example 1

Preparation of Dosing Solutions

GLP-1 was obtained from Bachem (Torrance, Calif.) as a bulk powder. To prepare stock solutions, GLP-1 was dissolved in deionized water (pH ~6.5) to obtain a concentration of 8 mg/ml. Stock solutions were kept frozen at $-20°$ C. in 0.5-ml aliquots until used. For dosing solutions, delivery agent was dissolved in deionized water to obtain a final concentration of 200 mg/ml (oral dosing) or 100 mg/ml (intracolonic dosing). The free acid form of delivery agent was converted to the sodium salt by adding one equivalent of sodium hydroxide. Solutions were vortexed, sonicated, and heated, and if necessary, additional sodium hydroxide was added in μl quantities to achieve uniform solubility. A specified quantity of GLP-1 stock was then added to the delivery agent solution to obtain a final concentration of 1 or 0.3 mg/ml (oral) or 0.6 mg/ml (intracolonic). After solubilization and drug addition, solutions were brought to final volume by the addition of deionized water.

Animals and Dosing

GLP-1 was administered to male, Sprague-Dawley rats either alone or in combination with an Emisphere delivery agent. Typically, rats were fasted for 18-24 hours prior to dosing. On the day of the experiment, rats were weighed and then anesthetized with a combination of ketamine (44 mg/kg) and thorazine (1.5 mg/kg).

Anesthesia was administered by intramuscular (IM) injection (26-gauge needle) into the hindleg in a volume of 0.5 mls/kg body weight. A tail or toe pinch was used to determine the level of anesthesia. Once anesthetized, rats were administered GLP-1 alone or in combination with an Emisphere delivery agent. Routes of delivery were either oral (PO) or intracolonic (IC). For PO & IC dosing, a Rusch 8 French catheter was cut to 11 cm in length and adapted to fit a 1-ml syringe. The syringe was filled with dosing solution and the catheter was wiped dry of excess solution. For PO dosing, the catheter was inserted into the rat mouth and fed down the esophagus (10.0 cm). The dosing solution was delivered by pressing the syringe plunger while holding the rat in an upright position. The doses of delivery agent and CUP-1 were 200 mg/kg and 1 or 0.3 mg/kg, respectively. The dose volume was 1 ml/kg. For IC dosing, the catheter was inserted into the rectum and fed into the colon (7.5 cm). The dosing solution was delivered by pressing the syringe plunger while holding the rat up by the tail. The doses of delivery agent and GLP-1 were 50 mg/kg and 0.3 mg/kg, respectively. The dose volume was 0.5 ml/kg.

Sample Collection and Handling

During blood sample collection, rats may have received additional injections of ketamine/thorazine in order to maintain anesthesia. For blood sampling, a 22-gauge needle was inserted into the tail artery. Typically, blood samples were collected prior to dosing (time 0) and at 5, 15, 30, 45, and 60 minutes after dosing. Samples were collected into capiject tubes containing EDTA and a DDP-IV inhibitor, and placed on wet ice until centrifugation. After all samples were collected, tubes were centrifuged at 10,000 rpm for 4 minutes at $4°$ C. in order to separate the plasma. Plasma was collected into eppendorf tubes and frozen at $-20°$ C. until assayed.

Bioanalytical Method and Data Analysis

Briefly, concentrations of GLP-1 were quantified in rat plasma using a radioimmunoassay (RIA). The % $B/B_0$ (% bound drug/unbound drug) was derived for the assay standards and plotted on a log/log scale. A 4 PL logistic fit was used to fit the standard curve. The sample concentrations were calculated by reading the % $B/B_0$ of the samples off the standard curve. % $B/B_0$ values from each time point were averaged (n=5) and plotted versus concentration, Finally, data were expressed as mean plasma concentration of GLP-1 (±SEM) versus time. The range of the assay was 0.1-12.8 ng/ml.

The results are shown in Table 2,

TABLE 2

| Delivery Agent | Compound Dose | Compound Dose Unit | Drug Dose | Drug Dose Unit | Test Article Viscosity | Dose Volume | Dose Volume Unit | pH | CMAX | Std. Dev. | TMAX |
|---|---|---|---|---|---|---|---|---|---|---|---|
| N/A | 0 | mg/kg | 1 | ng/kg | Solution | 0.5 | mL/kg | 8.15 | 31.44 | 17.5 | 60 |
| N/A | 0 | mg/kg | 2 | ng/kg | Solution | 0.5 | mL/kg | 7.2 | 32.37 | 18.75 | 45 |
| N/A | 0 | mg/kg | 3 | ng/kg | Solution | 0.5 | mL/kg | 7.41 | 17.47 | 22.85 | 45 |
| N/A | 0 | mg/kg | 30 | ng/kg | Solution | 0.5 | mL/kg | 7.41 | 19.17 | 17.7 | 45 |
| N/A | 0 | mg/kg | 10 | ng/kg | Solution | 0.5 | mL/kg | 7.41 | 17.06 | 8.41 | 45 |
| N/A | 0 | mg/kg | 50 | ng/kg | Solution | 0.5 | mL/kg | 7.42 | 152.8 | 179.31 | 15 |
| N/A | 0 | mg/kg | 500 | μg/kg | Solution | 1 | mL/kg | 7.42 | 106.03 | 74.33 | 15 |
| N/A | 0 | ng/kg | 30 | ng/kg | Solution | 0.5 | mL/kg | 7 | 64.44 | 41.48 | 15 |
| N/A | 0 | mg/kg | 0 | ng/kg | Solution | 0.5 | mL/kg | 7.21 | 11.68 | 2.04 | 30 |
| N/A | 0 | mg/kg | 300 | μg/kg | Solution | 1 | mL/kg | 7.78 | 64.2 | 24 | 15 |

TABLE 2-continued

| Delivery Agent | Compound Dose | Compound Dose Unit | Drug Dose | Drug Dose Unit | Test Article Viscosity | Dose Volume | Dose Volume Unit | pH | CMAX | Std. Dev. | TMAX |
|---|---|---|---|---|---|---|---|---|---|---|---|
| N/A | 0 | ng/kg | 30 | ng/kg | Solution | 0.5 | mL/kg | 7.3 | 6.4 | 6.46 | 15 |
| N/A | 0 | mg/kg | 0 | ng/kg | Solution | 0.5 | mL/kg | 7.26 | 11.13 | 12.38 | 30 |
| N/A | 0 | mg/kg | 300 | µg/kg | Solution | 1 | mL/kg | 7.28 | 26.54 | 20.9 | 15 |
| N/A | 0 | mg/kg | 0 | ng/kg | Solution | 0.5 | mL/kg | 7.84 | 0.06 | 0.2 | 60 |
| N/A | 0 | mg/kg | 0 | ng/kg | Solution | 1 | mL/kg | 7.54 | 5.87 | 3.01 | 5 |
| N/A | 0 | mg/kg | 0.3 | mg/kg | Solution | 0.5 | mL/kg | 7.29 | 20016.87 | 1902.17 | 5 |
| N/A | 0 | mg/kg | 0.5 | mg/kg | Solution | 0.5 | mL/kg | 7.29 | 27881.88 | 3169.1 | 5 |
| N/A | 0 | mg/kg | 0.3 | mg/kg | Solution | 0.5 | mL/kg | 7.22 | 7296.44 | 0 | 30 |
| N/A | 200 | mg/kg | 1 | mg/kg | Solution | 1 | mL/kg | 8.26 | 5263.6 | 3269.83 | 30 |
| 1 | 200 | mg/kg | 1 | mg/kg | Thick Suspension | 1 | mL/kg | 8.59 | 6416.4 | 4602.7 | 5 |
| 2 | 200 | mg/kg | 100 | µg/kg | Solution | 1 | mL/kg | 7.79 | 27.37 | 10.72 | 45 |
| 2 | 100 | mg/kg | 1 | ng/kg | Solution | 0.5 | mL/kg | 7.82 | 251.05 | 10.44 | 45 |
| 2 | 200 | mg/kg | 300 | µg/kg | Solution | 1 | mL/kg | 7.9 | 33.65 | 28.1 | 15 |
| 2 | 100 | mg/kg | 50 | ng/kg | Solution | 0.5 | mL/kg | 7.8 | 172.3 | 120.36 | 15 |
| 2 | 200 | mg/kg | 500 | µg/kg | Solution | 1 | mL/kg | 7.9 | 191.28 | 99.9 | 15 |
| 2 | 200 | mg/kg | 500 | µg/kg | Solution | 1 | mL/kg | 8.02 | 202.37 | 131.63 | 5 |
| 2 | 200 | mg/kg | 300 | µg/kg | Solution | 1 | mL/kg | 8.03 | 272.32 | 161.13 | 5 |
| 2 | 200 | mg/kg | 300 | µg/kg | Solution | 1 | mL/kg | 7.93 | 142.47 | 83.57 | 5 |
| 2 | 200 | mg/kg | 300 | µg/kg | Solution | 1 | mL/kg | 7.93 | 62.15 | 46.21 | 5 |
| 2 | 200 | mg/kg | 300 | µg/kg | Solution | 1 | mL/kg | 7.96 | 116.87 | 64.73 | 5 |
| 2 | 200 | mg/kg | 300 | µg/kg | Solution | 1 | mL/kg | 7.95 | 237.61 | 14.42 | 5 |
| 2 | 200 | mg/kg | 300 | µg/kg | Solution | 1 | mL/kg | 0 | 184.53 | 150.25 | 5 |
| 2 | 200 | mg/kg | 0 | ng/kg | Solution | 1 | mL/kg | 7.87 | 0.39 | 0.75 | 0 |
| 2 | 200 | mg/kg | 0 | ng/kg | Solution | 1 | mL/kg | 7.85 | 4.19 | 3.45 | 0 |
| 2 | 200 | mg/kg | 0.3 | mg/kg | Solution | 1 | mL/kg | 7.88 | 6255.93 | 2047.75 | 5 |
| 2 | 200 | mg/kg | 1 | mg/kg | Solution | 1 | mL/kg | 7.98 | 16883.03 | 3547.16 | 5 |
| 2 | 200 | mg/kg | 0 | mg/kg | Solution | 1 | mL/kg | 7.77 | 4449.6 | 164.81 | 60 |
| 2 | 50 | mg/kg | 0.3 | mg/kg | Solution | 0.5 | mL/kg | 7.7 | 192683.8 | 52728.26 | 5 |
| 2 | 200 | mg/kg | 1 | mg/kg | Solution | 1 | mL/kg | 8.05 | 63731.12 | 113564.6 | 5 |
| 2 | 200 | mg/kg | 1 | mg/kg | Solution | 1 | mL/kg | 7.85 | 16120.01 | 2846.6 | 5 |
| 2 | 200 | mg/kg | 1 | mg/kg | Solution | 1 | mL/kg | 8.23 | 10085.71 | 8026.96 | 5 |
| 2 | 200 | mg/kg | 1 | mg/kg | Solution | 1 | mL/kg | 8 | 220007 | 9701.94 | 5 |
| 2 | 200 | mg/kg | 1 | mg/kg | Solution | 1 | mL/kg | 7.99 | 21676.09 | 31312.22 | 5 |
| 2 | 200 | mg/kg | 1 | mg/kg | Solution | 1 | mL/kg | 8.09 | 27297.38 | 32710.69 | 5 |
| 2 | 200 | mg/kg | 1 | mg/kg | Solution | 1 | mL/kg | 7.93 | 8794.6 | 10125 | 5 |
| 2 | 200 | mg/kg | 1 | mg/kg | Solution | 1 | mL/kg | 8.11 | 7944.47 | 656.06 | 30 |
| 2 | 200 | mg/kg | 1 | mg/kg | Solution | 1 | mL/kg | 7.94 | 14638.04 | 9393.71 | 5 |
| 2 | 200 | mg/kg | 1 | mg/kg |  | 1 | mL/kg | 7.84 | 19262.84 | 11361.48 | 5 |
| 2 | 200 | mg/kg | 1 | mg/kg |  | 1 | mL/kg | 7.84 | 10927.55 | 9295.88 | 5 |
| 3 | 200 | mg/kg | 1 | mg/kg | Suspension | 1 | mL/kg | 7.83 | 2918.87 | 3456.52 | 15 |
| 4 | 200 | mg/kg | 300 | µg/kg | Suspension | 1 | mL/kg | 7.26 | 53.44 | 22 | 60 |
| 4 | 200 | mg/kg | 1 | mg/kg | Suspension | 1 | mL/kg | 7.69 | 2897.81 | 935.84 | 60 |
| 5 | 200 | mg/kg | 300 | µg/kg | Solution | 1 | mL/kg | 7.48 | 245.18 | 132.51 | 5 |
| 6 | 200 | mg/kg | 300 | µg/kg | Solution | 1 | mL/kg | 7.29 | 79.06 | 94.86 | 15 |
| 6 | 200 | mg/kg | 1 | mg/kg | Suspension | 1 | mL/kg | 7.05 | 8557 | 4877.95 | 5 |
| 7 | 200 | mg/kg | 1 | mg/kg | Precipitate | 1 | mL/kg | 7.99 | 119647.6 | 97637.84 | 5 |
| 7 | 200 | mg/kg | 1 | mg/kg | Solution | 1 | mL/kg | 8.06 | 8179.44 | 3662.2 | 5 |
| 7 | 200 | mg/kg | 1 | mg/kg | Solution | 1 | mL/kg | 8.14 | 8875.04 | 2822.07 | 5 |
| 8 | 200 | mg/kg | 1 | mg/kg |  | 1 | mL/kg | 9.21 | 6034.29 | 6986.65 | 5 |
| 9 | 200 | mg/kg | 1 | mg/kg | Suspension | 1 | mL/kg | 8.04 | 8623.09 | 4623.85 | 30 |
| 10 | 200 | mg/kg | 300 | µg/kg | Suspension | 1 | mL/kg | 7.23 | 128.77 | 41.23 | 45 |
| 10 | 200 | mg/kg | 1 | mg/kg |  | 1 | mL/kg | 7.54 | 26149.3 | 16719.87 | 6 |
| 11 | 200 | mg/kg | 1 | mg/kg | Suspension | 1 | mL/kg | 8.17 | 56735.66 | 74607.84 | 15 |
| 11 | 200 | mg/kg | 1 | mg/kg | Suspension | 1 | mL/kg | 7.98 | 10706.06 | 9289.96 | 5 |
| 11 | 200 | mg/kg | 1 | mg/kg | Suspension | 1 | mL/kg | 8.08 | 6282.66 | 2692.72 | 5 |
| 12 | 200 | mg/kg | 1 | mg/kg | Suspension | 2 | mL/kg | 8.72 | 1614.27 | 1366.02 | 0 |
| 13 | 200 | mg/kg | 1 | mg/kg |  | 1 | mL/kg | 8.25 | 14251.93 | 4639.93 | 5 |
| 14 | 200 | mg/kg | 1 | mg/kg |  | 1 | mL/kg | 7.92 | 9698.55 | 11222.76 | 15 |
| 15 | 200 | mg/kg | 1 | mg/kg |  | 1 | mL/kg | 7.2 | 3490.73 | 226.73 | 60 |
| 16 | 200 | mg/kg | 500 | µg/kg | Solution | 1 | mL/kg | 7.63 | 276.71 | 179.56 | 5 |
| 16 | 200 | mg/kg | 1 | mg/kg | Precipitate | 1 | mL/kg | 7.46 | 25042.82 | 27608.88 | 5 |
| 16 | 200 | mg/kg | 1 | mg/kg | Suspension | 1 | mL/kg | 7.54 | 10087.13 | 10062.1 | 5 |
| 16 | 200 | mg/kg | 1 | mg/kg |  | 1 | mL/kg | 7.55 | 9066.14 | 5339.88 | 5 |
| 17 | 200 | mg/kg | 1 | mg/kg | Solution | 1 | mL/kg | 7.99 | 5579.88 | 5326.24 | 5 |
| 18 | 200 | mg/kg | 300 | µg/kg | Solution | 1 | mL/kg | 7.25 | 187.05 | 125.1 | 5 |
| 18 | 200 | mg/kg | 1 | mg/kg | Solution | 1 | mL/kg | 7.36 | 9178.62 | 11198.92 | 5 |
| 18 | 200 | mg/kg | 1 | mg/kg | Solution | 1 | mL/kg | 6.83 | 15291.42 | 11361.22 | 5 |
| 19 | 200 | mg/kg | 500 | µg/kg | Suspension | 1 | mL/kg | 7.62 | 265.16 | 97.36 | 5 |
| 19 | 200 | mg/kg | 1 | mg/kg | Precipitate | 1 | mL/kg | 7.77 | 68658.34 | 139711.8 | 15 |
| 19 | 200 | mg/kg | 1 | mg/kg | Suspension | 1 | mL/kg | 7.58 | 6302.52 | 7470.2 | 5 |
| 19 | 200 | mg/kg | 1 | mg/kg | Solution | 1 | mL/kg | 6.95 | 9909.15 | 11124.83 | 5 |
| 19 | 200 | mg/kg | 1 | mg/kg |  | 1 | mL/kg | 7.49 | 36376.31 | 38377.66 | 5 |
| 20 | 200 | mg/kg | 1 | mg/kg | Solution | 1 | mL/kg | 8.09 | 7960.59 | 4935.56 | 30 |
| 21 | 200 | mg/kg | 300 | µg/kg | Solution | 1 | mL/kg | 0 | 54.86 | 72.09 | 15 |
| 22 | 200 | mg/kg | 1 | mg/kg | Solution | 1 | mL/kg | 12.3 | 3307.93 | 4007.28 | 5 |
| 23 | 200 | mg/kg | 300 | µg/kg | Suspension | 1 | mL/kg | 7.57 | 68.37 | 52.78 | 5 |

TABLE 2-continued

| Delivery Agent | Compound Dose | Compound Dose Unit | Drug Dose | Drug Dose Unit | Test Article Viscosity | Dose Volume | Dose Volume Unit | pH | CMAX | Std. Dev. | TMAX |
|---|---|---|---|---|---|---|---|---|---|---|---|
| 24 | 200 | mg/kg | 300 | μg/kg | Suspension | 1 | mL/kg | 11.42 | 263.88 | 140.25 | 15 |
| 24 | 200 | mg/kg | 1 | mg/kg | Solution | 1 | mL/kg | 11.64 | 54205.73 | 107148.1 | 15 |
| 24 | 200 | mg/kg | 1 | mg/kg | Suspension | 1 | mL/kg | 11.46 | 11323.24 | 16079.29 | 5 |
| 24 | 200 | mg/kg | 1 | mg/kg | Solution | 1 | mL/kg | 11.42 | 23859.27 | 13054.48 | 5 |
| 24 | 200 | mg/kg | 1 | mg/kg | | 1 | mL/kg | 11.4 | 16166.59 | 7698.96 | 5 |
| 25 | 200 | mg/kg | 300 | μg/kg | Suspension | 1 | mL/kg | 0 | 49.88 | 47.1 | 5 |
| 26 | 200 | mg/kg | 1 | mg/kg | Solution | 1 | mL/kg | 10.96 | 1111.87 | 1744.86 | 5 |
| 27 | 200 | mg/kg | 300 | μg/kg | Solution | 1 | mL/kg | 10.43 | 72.8 | 53.13 | 15 |
| 28 | 200 | mg/kg | 1 | mg/kg | Suspension | 2 | mL/kg | 3.02 | 3234.77 | 1370.25 | 5 |
| 29 | 200 | mg/kg | 1 | mg/kg | Solution | 1 | mL/kg | 3.34 | 2748.78 | 800.51 | 45 |

Example 2

Preparation of Deliver Agent No. 24 in Published International Application No. 03/072195

Preparation of 4-dimethylamino-benzoyl chloride

To a 1000 mL round bottomed flask was added 4-dimethylamino-benzoic acid (50.0 g, 1.0 eq) and THF (600 mL). A solution of thionyl chloride (44.16 mL, 2.0 eq) in tetrahydrofuran was added and the resulting mixture heated to reflux for 4 hours. The excess thionyl chloride and solvent were removed under reduced pressure to yield 4-dimethylamino-benzoyl chloride as a solid, which was used without further purification in the preparation of compound 560.

Preparation of delivery agent 24: To a 1000 mL round bottomed flask was added chlorotrimethylsilane (15.48 mL, 2 eq) in methylene chloride (250 ml). 4-aminobutyric acid (10.0 g, 1 equivalent) was added and the mixture was heated to reflux for 1.5 hours. The resulting solution was cooled to 0° C. (ice bath) and triethylamine (27.21 mL, 3 equivalents) was added drop-wise. A solution of 4-dimethylamino-benzoyl chloride (11.12 g, 1 eq) in methylene chloride (50 mL) was added drop-wise to the resulting reaction mixture over 0.5 hours. The temperature was maintained at 0° C. (ice bath) during the addition and for 0.5 hour after the addition was complete. The solution was allowed to warm to ambient temperature. Chloroform (25 mL) was added to improve the solubility of the reactants. The reaction was complete (as indicated by TLC) after 16.5 hours. The solvents were removed under reduced pressure. The resulting solid was dissolved in ethyl acetate (500 mL) and 2.5% aqueous sodium bicarbonate (500 mL) was added. The aqueous layer was acidified to pH 6.5 with aqueous sulfuric acid (2 M) and extracted with ethyl acetate (three times 500 mL). After each extraction, the pH of the aqueous layer was adjusted to pH 6.5. The combined ethyl acetate fractions were dried over sodium sulfate. The sodium sulfate was removed by filtration and the solvent removed under reduced pressure. The crude product was recrystallized from methanol/water and dried under reduced pressure to yield compound 560 (4.97 g, approximately 25% overall yield).

Example 3

Preparation of Deliver Agent No. 8 in Published International Application No. 03/072195

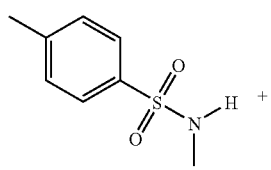

-continued

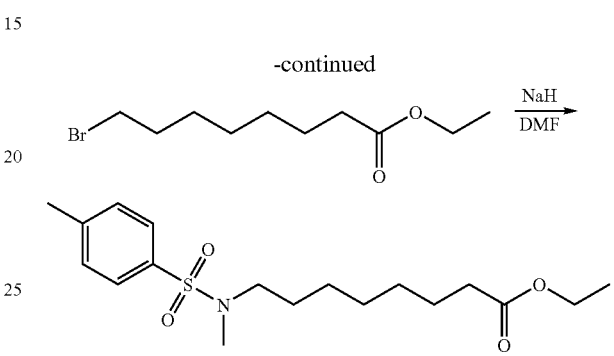

Step 1. 4,N-Dimethylbenzenesulphonamide was reacted with ethyl-8-bromooctanoate in DMF under the influence of sodium hydride to obtain 8-[Methyl-(toluene-4-sulfonyl)-amino]-octanoic acid ethyl ester

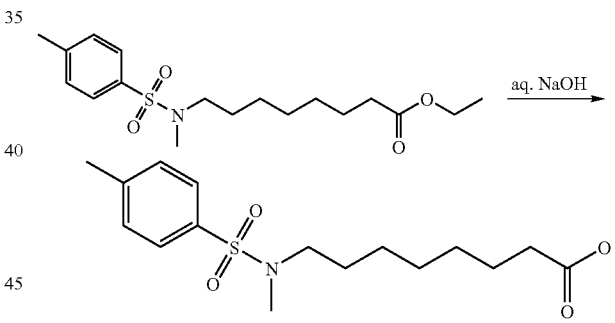

Step 2. The ester of 8-[Methyl-(toluene-4-sulfonyl)-amino]-octanoic acid ethyl ester was hydrolyzed in aqueous sodium hydroxide to obtain 8-[Methyl-(toluene-4-sulfonyl)-amino]-octanoic acid

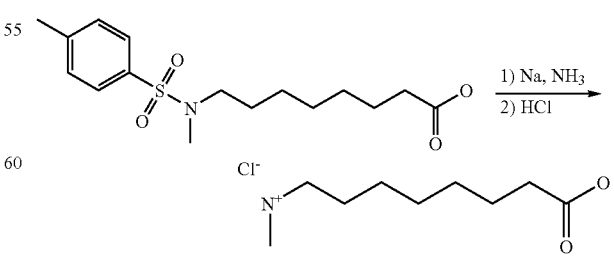

Step 3. The sulphonamide of 8-[Methyl-(toluene-4-sulfonyl)-amino]-octanoic acid was removed under reductive conditions and the resulting amine reacted with hydrogen chloride to obtain (7-Carboxy-heptyl)-methylammonium hydrochloride.

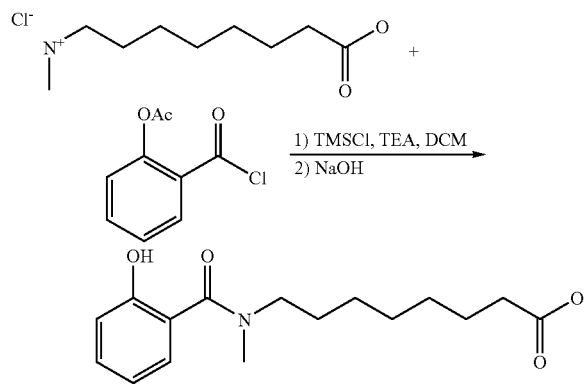

Step 4. The carboxylic acid of (7-Carboxy-heptyl)-methylammonium hydrochloride was protected in-situ with chlorotrimethylsilane. The resulting trimethylsilyl ester was reacted with O-acetylsalicyloyl chloride. The protecting groups were removed with aqueous sodium hydroxide, and after extensive purification, 8-[(2-Hydroxy-benzoyl)-methyl-amino]-octanoic acid, was obtained.

One equivalent each reactants plus 2 equivalents TMSCl plus 2.5 equivalents TEA and MeCl were placed in a 250 ml round bottomed flask fitted with N2 purge, magnetic stir bar and condenser. TMSCl was added. Heating was begun The reaction mixture was refluxing in an oil bathe temperature of 50 C after about ½ hour. Heating was stopped after about 2 hours and the reaction mixture placed in an ice/H2O bath. TEA was added. ASCC was dissolved in 10 ml MeCl2. This was placed in a 60 ml addition funnel atop flask. Dropwise addition was begun. Addition was completed after about ½ hour. The ice bath was removed. Methylene chloride was removed under vacuum, 2N NaOH was added. This was allowed to stir for several hours. Then 2N HCl was added. A yellow oil separated out.

The mixture was extracted 3×100 ml EtOAc. EtOAc was dried with Na2SO4 and concentrated under vacuum. A yellow oil (A) is obtained, 2N NaOH was added to 250 ml round bottom flask containing the yellow oil, the mixture was allowed to stir over the weekend. The mixture was filtered. A tan solid (B) was collected above filter. Below a clear filtrate collected. The filtrate was acidified with 2N HCl. A yellow oil separated. The mixture was extracted 3× with EtOAc. EtOAc is dried with Na2SO4 and concentrated under vacuum. A yellow oil remained (C). The oil was stirred in 40-50 C water bath. The aqueous layer was extracted with MeCl2, the MeCl2 was concentrated. A light brown oil was recovered. Oil was taken up in 2N NaOH. A cloudy mixture formed, which was acidified with 2NHCl to pH 5.4, 5.0 and 4.5. At each of these pus, the aqueous mixture was extracted with 3×50 ml portions EtOAc. The 5.4 and 5.0 fractions were combined, dried with Na2SO4 and concentrated under vacuum. A brown oil was obtained.

A number of fractions were found to contain the desired product. These were dissolved in $MeC_{l2}$ and combined. $MeC_{l2}$ was removed under vacuum. A brown oil remained, which was taken up in MeOH. Several drops concentrated sulfuric acid were added and the solution allowed to reflux several hours. LC indicated reaction to prepare methyl ester had gone to completion. Heating was stopped. Several mgs sodium bicarbonate were added and MeOH removed under vacuum. The residue was taken up in EtO and extracted first with 2×50 ml portions SAT sodium bicarbonate and then 2×50 ml portions brine. Ether was concentrated and a brown oil remained. The oil was placed on a silica gel column and eluted through column with 70:30 hexane:EtOAc. 100 ml fractions taken. Fractions found to contain desired product by TLC were combined and concentrated. A light colored oil remained. Oil was taken up in about 50 ml 12N NaOH. This was stirred until LC indicated a shift due to hydrolysis of Me ester. The reaction mixture was acidified and a light colored oil separated out. The mixture was extracted with 3×50 ml portions EtOAc, EtOAc was dried with Na2SO4 and concentrated under vacuum.

NMR analysis of the oil (A) indicated the oil contained mostly the desired product. Some EtOAc was present. Upon sitting, the oil slowly solidified. It was placed in refrigeration for about 2 weeks when most had solidified. It was removed from refrigeration and stirred in warm water again. The water was decanted off leaving tall solid (B), which LC indicated contained mostly the desired product with some impurities. An attempt was made to recrystallize from 70:30 Hexane:EtOAc Overnight a tan solid (C) precipitated. This was isolated by filtration and allowed to dry under vacuum overnight. LC of (C) indicated single peak at 4.53. Samples were submitted for analysis, and results were 180C was recrystallized from 70:30 hexane:EtOAc. An oil (180D) separated out, and was taken and isolated. The oil was allowed to stand in a refrigerator. The oil (180D) had begun to crystallize it was allowed to continue to stand in refrigerator. The oil 180D was isolated and some liquid still remained. 180D had a strong acetic acid smell. This was washed several times with $H_2O$. A tall solid (180E) is isolated. 180E was dried under vacuum overnight. NMR was consistent with desired product. CHN theoretical C=65.31, H=7.82, N4.76, actual C=65.13, H=8.02, N=4.71. 180E was combined with an earlier fraction and designated as 18° F. yield 21.95 g.

180F: Yield 2.95 g. Molecular formula $C_{16}H_{23}NO_4$.

Molecular weight 293 g/mol. Melting point=85-88 C. Elemental analysis theoretical: C=65.31, H=7.82, N=−4.76. found: C=65.44, H=7.93, N=4.66.

Example 4

Preparation of Deliver Agent No. 8 in Published International Application No. 03/072195

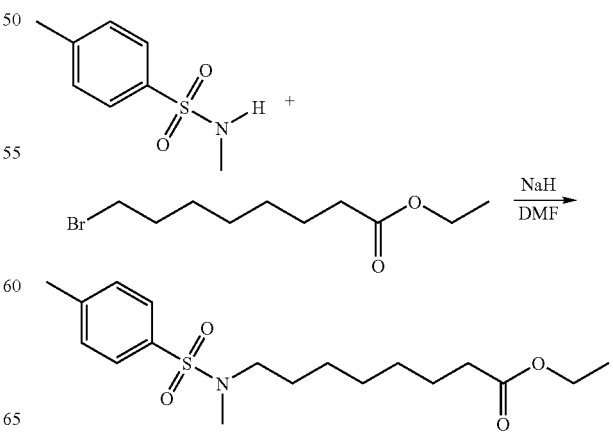

Step 1. 4,N-Dimethylbenzenesulphonamide was reacted with ethyl-8-bromooctanoate in DMF under the influence of sodium hydride to obtain 8-[Methyl-(toluene-4-sulfonyl)-amino]-octanoic acid ethyl ester Preparation of 8-[Methyl-(toluene-4-sulfonyl)-amino]-octanoic acid ethyl ester: A 500 ml round-bottomed flask equipped with nitrogen purge, magnetic stirbar, and a thermometer was charged with sodium hydride (3.11 g, 0.1297 mol, 1.2 eq) and DMF (30 ml), N-methyl-p-toluenesulphonamide (20.0 g, 0.1081 mol, 1.0 eq) was placed in a 125 ml Erlenmeyer flask and dissolved in DMF (50 ml). The N-methyl-p-toluenesulphonamide solution was added to the sodium hydride mixture dropwise with stirring over the course of approximately 45 min. A water bath was used to maintain the reaction temperature between 23 and 40° C. The resulting reaction mixture was heated to 43° C. for approximately 30 min. in a separate flask, ethyl-8-bromooctanoate (27.14 g, 0.1081 mol, 1.0 eq) was dissolved in DMF (150 ml). The solution of bromoester was added to the reaction mixture dropwise via addition funnel over the course of about 30 min. The reaction was maintained at approximately 58° C. during the addition. The reaction was cooled, and LC indicated completion by one predominant peak corresponding to product. The reaction mixture was poured into ice water (300 ml). The aqueous mixture was extracted with EtOAc (3×200 ml). The combined EtOAc layers were extracted with deionized water (3×200 ml), dried over Na$_2$SO$_4$, concentrated under reduced pressure, then placed under high vacuum overnight to yield 36.14 g of crude product. The crude product was chromatographed over silica gel in three portions. Each column was eluted with 80:20 hexane:EtOAc and 125 ml fractions collected. Appropriate product-containing fractions were combined, concentrated under reduced pressure, and further dried under high vacuum. LC and NMR indicated pure product from each of the three columns for a combined yield of 30.21 g 8-[methyl-(toluene-4-sulfonyl)-amino]-octanoic acid ethyl ester (0.0849 mol, 78.6% yield).

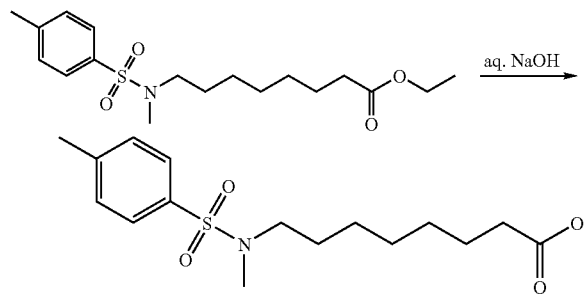

Step 2. The ester of 8-[Methyl-(toluene-4-sulfonyl)-amino]-octanoic acid ethyl ester was hydrolyzed in aqueous sodium hydroxide to obtain 8-[Methyl-(toluene-4-sulfonyl)-amino]-octanoic acid Preparation of 8-[methyl-(toluene-4-sulfonyl)-amino]-octanoic acid: To a 250 ml round bottomed flask fitted with nitrogen purge and magnetic stir bar was added 8-[methyl-(toluene-4-sulfonyl)-amino]-octanoic acid ethyl ester (10.21 g, 0.0288 mol, 1 eq) and 2N aq. NaOH (57.52 ml, 0.1150 mol, 4.0 eq). The resulting reaction mixture was allowed to stir overnight at ambient temperature. HPLC at this stage still indicated 2 peaks. The reaction mixture was heated to reflux for approximately 6 h, when HPLC indicated reaction was complete, the heat was turned off and the reaction allowed to cool to ambient temperature overnight. The hazy reaction mixture was acidified with 2N aq. HCl. A white oil separated. The reaction mixture was stirred vigorously in an ice bath and a solid white precipitate formed. The solid was isolated by filtration and dried under vacuum overnight. HPLC indicated a single peak, rt 6.44 min, and NMR was consistent with desired product 8-[methyl-(toluene-4-sulfonyl)-amino]-octanoic acid: 9.29 g, 0.0284 mol, 98.6% yield.

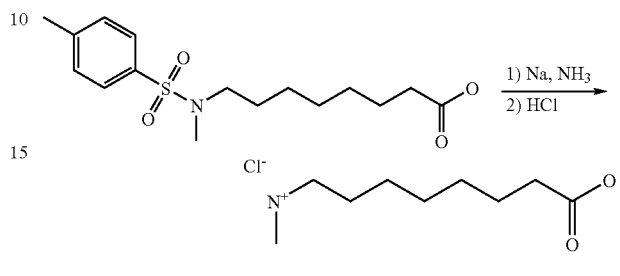

Step 3. The sulphonamide of 8-[Methyl-(toluene-4-sulfonyl)-amino]-octanoic acid was removed under reductive conditions and the resulting amine reacted with hydrogen chloride to obtain (7-Carboxy-heptyl)-methylammonium hydrochloride.

Preparation of (7-carboxy-heptyl)-methylammonium hydrochloride: To a 1000 ml round bottomed flask equipped with a dry ice condenser, nitrogen bubbler, ammonia inlet, and mechanical stirrer was added 8-[methyl-(toluene-4-sulfonyl)-amino]-octanoic acid (9.29 g, 0.0284 mol, 1.0 eq) and THF (20 ml). The mixture was cooled in a dry ice/acetone bath with stirring. Ammonia (ca. 300 ml) was condensed into the flask. Sodium (ca. 3.92 g, 0.1705 mol, 6 eq) was added portion-wise until the blue-green color persisted. Ammonium chloride was added until the reaction mixture appeared white. The dry ice/acetone condenser was removed and the ammonia allowed to boil off overnight. A white solid remained in the flask. Water (10 mls) was added and the mixture was acidified to pH 2-3 by addition of 2N HCl. At this point an oil separated out. The THF was removed under reduced pressure and the aqueous mixture was stirred for ca. 1 h at ambient temperature. Dichloromethane (50 ml) was added and the solid (product A) was filtered off. The remaining aqueous filtrate was concentrated under reduced pressure to obtain another white solid (product B). NOR analysis indicated that product A is the starting material, 8-[methyl-(toluene-4-sulfonyl)-amino]-octanoic acid, and product B is the desired product, (7-carboxy-heptyl)-methylammonium hydrochloride. The amount of product obtained was greater than 100% of the theoretical mass. Based on the assumption that the product contains sodium chloride and mass balance of recovered starting material, it was assumed the crude product contained 3.72 g of the desired product and it was carried on without further purification.

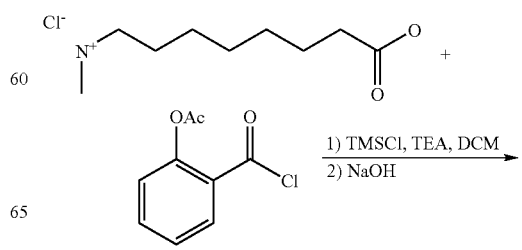

-continued

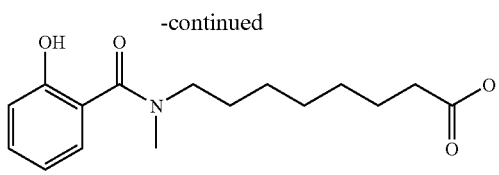

Step 4. The carboxylic acid of (7-Carboxy-heptyl)-methylammonium hydrochloride was protected in-situ with chlorotrimethylsilane. The resulting trimethylsilyl ester was reacted with O-acetylsalicyloyl chloride. The protecting groups were removed with aqueous sodium hydroxide, and after extensive purification, 8-[(2-Hydroxy-benzoyl)-methyl-amino]-octanoic acid, was obtained.

Preparation of 8-[(2-Hydroxy-benzoyl)-methyl-amino]-octanoic acid: To a 100 ml round bottomed flask fitted with argon purge, magnetic stir bar and condenser was added (7-carboxy-heptyl)-methylammonium hydrochloride (3.25 g, 0.0155 mol, 1.0 eq) and dichloromethane (DCM, 50 ml). Chlorotrimethylsilane (3.37 g, 0.0310 mol, 2.0 eq) was added and the resulting mixture was brought to reflux for approximately 2 h. The flask was removed from the heating mantle and placed in an ice water bath. Once the reaction was cooled to 0° C., triethylamine (3.92 g, 0.0388 mol, 2.5 eq) was added and a white vapor formed over the reaction mixture. The reaction was allowed to stir for approximately 10 min at 0° C. In a separate flask, acetylsalicyloyl chloride (ASCC, 3.08 g, 0.0155 mol, 1.0 eq) was dissolved in DCM (20 ml). The ASCC solution was added dropwise to the reaction mixture, the ice bath was removed, and the reaction mixture was allowed to stir and warm to ambient temperature overnight. The DCM was removed under reduced pressure and aqueous 2N NaOH (20 ml) was added to the residue. The aqueous mixture was allowed to stir at ambient temperature for several hours and was then acidified with aqueous 2N HCl. The aqueous mixture became cloudy and a brow oil separated out. The aqueous mixture was extracted with EtOAc (3×100 ml). The combined EtOAc extracts were combined, dried over $Na_2SO_4$, and concentrated under reduced pressure. The resulting brown oil was further dried under high vacuum to yield a brown solid. HPLC at this point indicated the solid consisted of two components (rt 2.8 min, salicylic acid and rt 4.0 min, desired product). This mixture was stirred in warm water (40-50° C.) to dissolve the salicylic acid. The remaining solid was filtered off, HPLC indicated this is predominantly desired product, crude yield 3.99 g (0.0136 mol, 87.7%). This material was treated in warm water (40-50° C.) and filtered two more times to produce pure 8-[(2-Hydroxy-benzoyl)-methyl-amino]-octanoic acid. (HPLC rt 4.0 min; NMR consistent with desired product; Elemental analysis Theoretical: C=65.31, H=7.82, N=4.76 Found: C=65.32, H=7.72, N=4.73) This application incorporates by reference in its entirety International Publication No. WO 03/072195, which is also attached as an appendix A to this application.

Throughout this description, the preferred embodiment and examples shown should be considered as exemplary, rather than as limitations on the present invention.

Unless defined other wise, all technical and scientific terms used herein have the same meaning as commonly understood by one of ordinary skill in the art to which the invention belongs. Any methods, compositions, reagents, cells, similar or equivalent to those described herein can be used in the practice or testing of the invention. All publications mentioned herein are incorporated herein, including all figures, graphs, equations, illustrations, and drawings, to describe and disclose specific information for which the reference was cited in connection with.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description. Patents, patent applications, publications, product descriptions, and protocols are cited throughout this application, the disclosures of which are incorporated herein by reference in their entireties for all purposes.

I claim:

1. A formulation comprising (i) a glucagon-like 1 peptide (GLP-1) compound having the amino acid sequence of SEQ ID NO: 2 and (ii) a delivery agent selected from the group consisting of

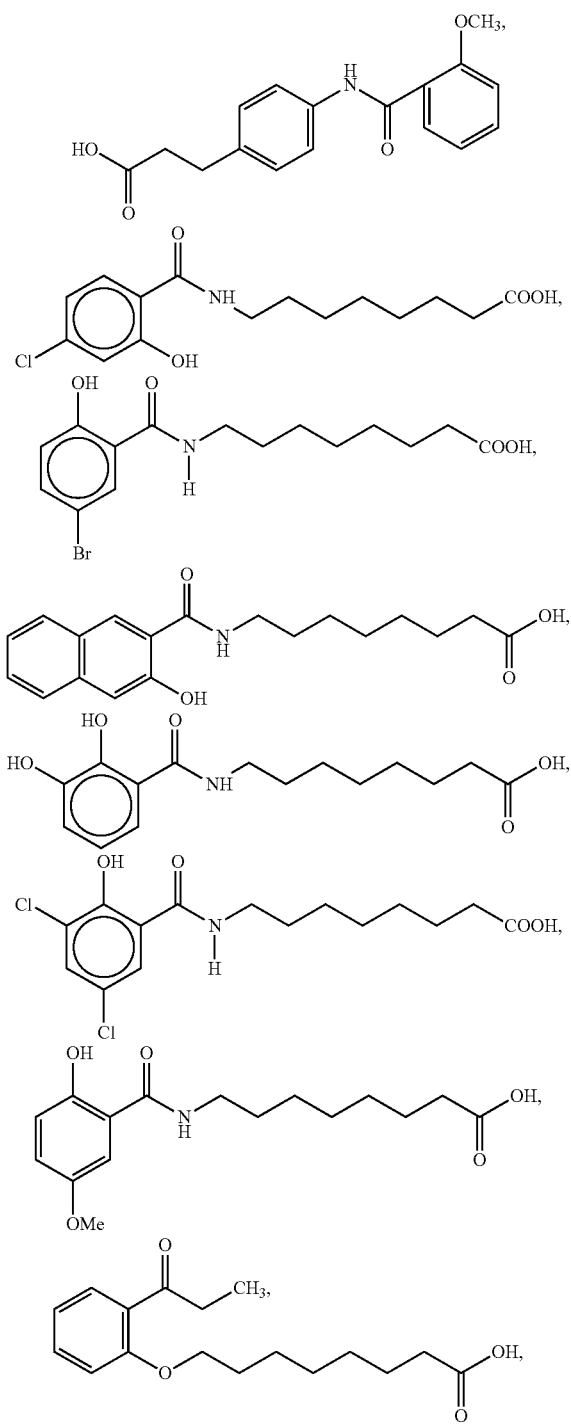
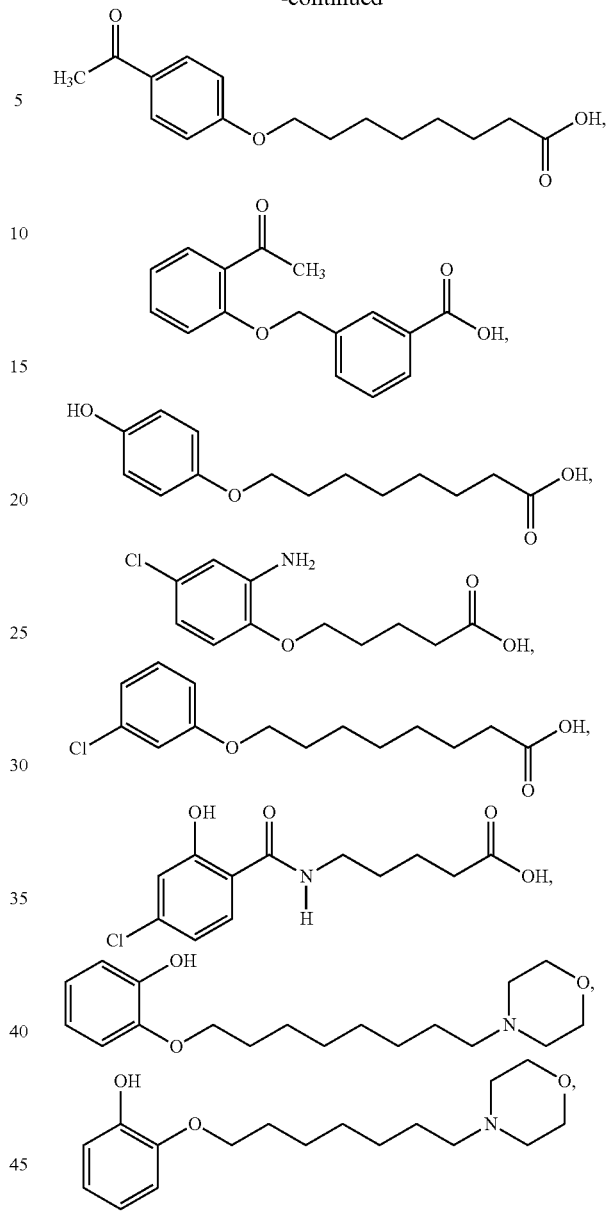

and pharmaceutically acceptable salts thereof.

2. The formulation of claim 1, further comprising an excipient selected from pharmaceutically acceptable buffers, suspending agents, co-solvents, preservatives, isotonicity agents, and combinations thereof.

3. The formulation of claim 1, in the form of a tablet, capsule or particle.

4. The formulation of claim 1, wherein the GLP-1 compound is a GLP-1 analog.

5. The formulation of claim 1, wherein the GLP-1 compound is a GLP-1 derivative.

6. The formulation of claim 1, wherein the GLP-1 compound is a GLP-1 fragment.

* * * * *

SEQUENCE LISTING

```
<160> NUMBER OF SEQ ID NOS: 16

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)
<223> OTHER INFORMATION: This residue may or may not be present
<220> FEATURE:
<223> OTHER INFORMATION: May or may not be c-term amidated

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala, Gly, Ser, Thr, Leu, Ile, Val, Glu, Asp, or
      Lys
<220> FEATURE:
<221> NAME/KEY: MOD_RES
<222> LOCATION: (3)
<223> OTHER INFORMATION: Glu, Asp, or Lys
<220> FEATURE:
<221> NAME/KEY: MOD_RES
<222> LOCATION: (5)
<223> OTHER INFORMATION: Thr, Ala, Gly, Ser, Leu, Ile, Val, Glu, Asp, or
      Lys
<220> FEATURE:
<221> NAME/KEY: MOD_RES
<222> LOCATION: (8)
<223> OTHER INFORMATION: Ser, Ala, Gly, Thr, Leu, Ile, Val, Glu, Asp, or
      Lys
<220> FEATURE:
<221> NAME/KEY: MOD_RES
<222> LOCATION: (10)
<223> OTHER INFORMATION: Val, Ala, Gly, Ser, Thr, Leu, Ile, Tyr, Glu,
      Asp, Trp, or Lys
<220> FEATURE:
<221> NAME/KEY: MOD_RES
<222> LOCATION: (11)
<223> OTHER INFORMATION: Ser, Ala, Gly, Thr, Leu, Ile, Val, Glu, Asp, or
      Lys
<220> FEATURE:
<221> NAME/KEY: MOD_RES
<222> LOCATION: (12)
<223> OTHER INFORMATION: Ser, Ala, Gly, Thr, Leu, Ile, Val, Glu, Asp,
      Trp, Tyr, or Lys
<220> FEATURE:
<221> NAME/KEY: MOD_RES
<222> LOCATION: (13)
<223> OTHER INFORMATION: Tyr, Phe, Trp, Glu, Asp, Gln, or Lys
<220> FEATURE:
<221> NAME/KEY: MOD_RES
<222> LOCATION: (14)
<223> OTHER INFORMATION: Leu, Ala, Gly, Ser, Thr, Ile, Val, Glu, Asp,
      Met, Trp, Tyr, or Lys
<220> FEATURE:
<221> NAME/KEY: MOD_RES
<222> LOCATION: (15)
<223> OTHER INFORMATION: Glu, Asp, or Lys
<220> FEATURE:
<221> NAME/KEY: MOD_RES
<222> LOCATION: (16)
<223> OTHER INFORMATION: Gly, Ala, Ser, Thr, Leu, Ile, Val, Glu, Asp, or
      Lys
<220> FEATURE:
<221> NAME/KEY: MOD_RES
<222> LOCATION: (17)
<223> OTHER INFORMATION: Gln, Asn, Arg, Glu, Asp, or Lys
<220> FEATURE:
<221> NAME/KEY: MOD_RES
<222> LOCATION: (18)
<223> OTHER INFORMATION: Ala, Gly, Ser, Thr, Leu, Ile, Val, Arg, Glu,
      Asp, or Lys
<220> FEATURE:
<221> NAME/KEY: MOD_RES
<222> LOCATION: (19)
<223> OTHER INFORMATION: Ala, Gly, Ser, Thr, Leu, Ile, Val, Glu, Asp, or
      Lys
<220> FEATURE:
<221> NAME/KEY: MOD_RES
<222> LOCATION: (20)
<223> OTHER INFORMATION: Lys, Arg, Gln, Glu, Asp, or His
<220> FEATURE:
<221> NAME/KEY: MOD_RES
<222> LOCATION: (21)
<223> OTHER INFORMATION: Leu, Glu, Asp, or Lys
```

-continued

```
<220> FEATURE:
<221> NAME/KEY: MOD_RES
<222> LOCATION: (24)
<223> OTHER INFORMATION: Ala, Gly, Ser, Thr, Leu, Ile, Val, Glu, Asp, or
      Lys
<220> FEATURE:
<221> NAME/KEY: MOD_RES
<222> LOCATION: (25)
<223> OTHER INFORMATION: Trp, Phe, Tyr, Glu, Asp, or Lys
<220> FEATURE:
<221> NAME/KEY: MOD_RES
<222> LOCATION: (26)
<223> OTHER INFORMATION: Leu, Gly, Ala, Ser, Thr, Ile, Val, Glu, Asp, or
      Lys
<220> FEATURE:
<221> NAME/KEY: MOD_RES
<222> LOCATION: (27)
<223> OTHER INFORMATION: Val, Gly, Ala, Ser, Thr, Leu, Ile, Glu, Asp, or
      Lys
<220> FEATURE:
<221> NAME/KEY: MOD_RES
<222> LOCATION: (28)
<223> OTHER INFORMATION: Asn, Lys, Arg, Glu, Asp, or His
<220> FEATURE:
<221> NAME/KEY: MOD_RES
<222> LOCATION: (29)
<223> OTHER INFORMATION: Gly, Ala, Ser, Thr, Leu, Ile, Val, Glu, Asp, or
      Lys
<220> FEATURE:
<221> NAME/KEY: MOD_RES
<222> LOCATION: (30)
<223> OTHER INFORMATION: Gly, Arg, Lys, Glu, Asp, or His
<220> FEATURE:
<221> NAME/KEY: MOD_RES
<222> LOCATION: (31)
<223> OTHER INFORMATION: Pro, Gly, Ala, Ser, Thr, Leu, Ile, Val, Glu,
      Asp, Lys, or not present
<220> FEATURE:
<221> NAME/KEY: MOD_RES
<222> LOCATION: (32)
<223> OTHER INFORMATION: Ser, Arg, Lys, Glu, Asp, His, or not present
<220> FEATURE:
<221> NAME/KEY: MOD_RES
<222> LOCATION: (33)
<223> OTHER INFORMATION: Ser, Arg, Lys, Glu, Asp, His, or not present
<220> FEATURE:
<221> NAME/KEY: MOD_RES
<222> LOCATION: (34)
<223> OTHER INFORMATION: Gly, Asp, Glu, Lys, or not present
<220> FEATURE:
<221> NAME/KEY: MOD_RES
<222> LOCATION: (35)
<223> OTHER INFORMATION: Ala, Phe, Trp, Tyr, Glu, Asp, Lys, or not
      present
<220> FEATURE:
<221> NAME/KEY: MOD_RES
<222> LOCATION: (36)
<223> OTHER INFORMATION: Ser, Pro, Lys, Glu, Asp, or not present
<220> FEATURE:
<221> NAME/KEY: MOD_RES
<222> LOCATION: (37)
<223> OTHER INFORMATION: Ser, Pro, Glu, Asp, Lys, or not present
<220> FEATURE:
<221> NAME/KEY: MOD_RES
<222> LOCATION: (38)
<223> OTHER INFORMATION: Gly, Pro, Glu, Asp, Lys, or not present
<220> FEATURE:
<221> NAME/KEY: MOD_RES
<222> LOCATION: (39)
<223> OTHER INFORMATION: Ala, Ser, Val, Glu, Asp, Lys, or not present
<220> FEATURE:
<223> OTHER INFORMATION: May or may not be c-term amidated

<400> SEQUENCE: 2

His Xaa Xaa Gly Xaa Phe Thr Xaa Asp Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa
```

20                  25                  30
Xaa Xaa Xaa Xaa Xaa Xaa Xaa
        35

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His, beta-
      hydroxy-His, homo-His, alpha-fluoromethyl-His, or
      alpha-methyl-His
<220> FEATURE:
<221> NAME/KEY: MOD_RES
<222> LOCATION: (2)
<223> OTHER INFORMATION: Gly, Ala, Val, Leu, Ile, Ser, or Thr
<220> FEATURE:
<221> NAME/KEY: MOD_RES
<222> LOCATION: (3)
<223> OTHER INFORMATION: Thr, Ser, Arg, Lys, Trp, Phe, Tyr, Glu, or His
<220> FEATURE:
<221> NAME/KEY: MOD_RES
<222> LOCATION: (5)
<223> OTHER INFORMATION: Asp, Glu, Arg, Thr, Ala, Lys, or His
<220> FEATURE:
<221> NAME/KEY: MOD_RES
<222> LOCATION: (6)
<223> OTHER INFORMATION: His, Trp, Phe, or Tyr
<220> FEATURE:
<221> NAME/KEY: MOD_RES
<222> LOCATION: (10)
<223> OTHER INFORMATION: Leu, Ser, Thr, Trp, His, Phe, Asp, Val, Tyr,
      Glu, or Ala
<220> FEATURE:
<221> NAME/KEY: MOD_RES
<222> LOCATION: (12)
<223> OTHER INFORMATION: His, Pro, Asp, Glu, Arg, Ser, Ala, or Lys
<220> FEATURE:
<221> NAME/KEY: MOD_RES
<222> LOCATION: (13)
<223> OTHER INFORMATION: Gly, Asp, Glu, Gln, Asn, Lys, Arg, or Cys
<220> FEATURE:
<221> NAME/KEY: MOD_RES
<222> LOCATION: (17)
<223> OTHER INFORMATION: His, Asp, Lys, Glu, Gln, or Arg
<220> FEATURE:
<221> NAME/KEY: MOD_RES
<222> LOCATION: (18)
<223> OTHER INFORMATION: Glu, Arg, Ala, or Lys
<220> FEATURE:
<221> NAME/KEY: MOD_RES
<222> LOCATION: (20)
<223> OTHER INFORMATION: Trp, Tyr, Phe, Asp, Lys, Glu, or His
<220> FEATURE:
<221> NAME/KEY: MOD_RES
<222> LOCATION: (21)
<223> OTHER INFORMATION: Ala, Glu, His, Phe, Tyr, Trp, Arg, or Lys
<220> FEATURE:
<221> NAME/KEY: MOD_RES
<222> LOCATION: (24)
<223> OTHER INFORMATION: Ala, Glu, Asp, Ser, or His
<220> FEATURE:
<221> NAME/KEY: MOD_RES
<222> LOCATION: (25)
<223> OTHER INFORMATION: Asp, Glu, Ser, Thr, Arg, Trp, or Lys
<220> FEATURE:
<221> NAME/KEY: MOD_RES
<222> LOCATION: (27)
<223> OTHER INFORMATION: Asp, Arg, Val, Lys, Ala, Gly, or Glu
<220> FEATURE:
<221> NAME/KEY: MOD_RES
<222> LOCATION: (28)

```
<223> OTHER INFORMATION: Glu, Lys, or Asp
<220> FEATURE:
<221> NAME/KEY: MOD_RES
<222> LOCATION: (29)
<223> OTHER INFORMATION: Thr, Ser, Lys, Arg, Trp, Tyr, Phe, Asp, Gly,
      Pro, His, or Glu
<220> FEATURE:
<221> NAME/KEY: MOD_RES
<222> LOCATION: (30)
<223> OTHER INFORMATION: Thr, Ser, Asp, Trp, Tyr, Phe, Arg, Glu, or His
<220> FEATURE:
<221> NAME/KEY: MOD_RES
<222> LOCATION: (31)
<223> OTHER INFORMATION: Lys, Arg, Thr, Ser, Glu, Asp, Trp, Tyr, Phe,
      His, Gly, or not present
<220> FEATURE:
<221> NAME/KEY: MOD_RES
<222> LOCATION: (32)
<223> OTHER INFORMATION: This residue may or may not be present; when
      present position 31 is Gly

<400> SEQUENCE: 3

Xaa Xaa Xaa Gly Xaa Xaa Thr Ser Asp Xaa Ser Xaa Xaa Leu Glu Gly
 1               5                  10                  15

Xaa Xaa Ala Xaa Xaa Phe Ile Xaa Xaa Leu Xaa Xaa Xaa Xaa Xaa Pro
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His, beta-
      hydroxy-His, homo-His, alpha-fluoromethyl-His,
      or ora-methyl-His
<220> FEATURE:
<221> NAME/KEY: MOD_RES
<222> LOCATION: (2)
<223> OTHER INFORMATION: Gly, Ala, Val, Leu, Ile, Ser, or Thr
<220> FEATURE:
<221> NAME/KEY: MOD_RES
<222> LOCATION: (5)
<223> OTHER INFORMATION: Asp, Glu, Arg, Thr, Ala, Lys, or His
<220> FEATURE:
<221> NAME/KEY: MOD_RES
<222> LOCATION: (6)
<223> OTHER INFORMATION: His, Trp, Phe, or Tyr
<220> FEATURE:
<221> NAME/KEY: MOD_RES
<222> LOCATION: (10)
<223> OTHER INFORMATION: Leu, Ser, Thr, Trp, His, Phe, Asp, Val, Glu, or
      Ala
<220> FEATURE:
<221> NAME/KEY: MOD_RES
<222> LOCATION: (16)
<223> OTHER INFORMATION: Gly, Asp, or Glu
<220> FEATURE:
<221> NAME/KEY: MOD_RES
<222> LOCATION: (17)
<223> OTHER INFORMATION: His, Asp, Lys, Glu, or Gln
<220> FEATURE:
<221> NAME/KEY: MOD_RES
<222> LOCATION: (18)
<223> OTHER INFORMATION: Glu, His, Ala, or Lys
<220> FEATURE:
<221> NAME/KEY: MOD_RES
<222> LOCATION: (19)
<223> OTHER INFORMATION: Asp, Lys, Glu, or His
<220> FEATURE:
<221> NAME/KEY: MOD_RES
<222> LOCATION: (21)
```

```
<223> OTHER INFORMATION: Ala, Glu, His, Phe, Tyr, Trp, Arg, or Lys
<220> FEATURE:
<221> NAME/KEY: MOD_RES
<222> LOCATION: (24)
<223> OTHER INFORMATION: Ala, Glu, Asp, Ser, or His
<220> FEATURE:
<221> NAME/KEY: MOD_RES
<222> LOCATION: (27)
<223> OTHER INFORMATION: Asp, Arg, Val, Lys, Ala, Gly, or Glu
<220> FEATURE:
<221> NAME/KEY: MOD_RES
<222> LOCATION: (28)
<223> OTHER INFORMATION: Glu, Lys, or Asp
<220> FEATURE:
<221> NAME/KEY: MOD_RES
<222> LOCATION: (29)
<223> OTHER INFORMATION: Thr, Ser, Lys, Arg, Trp, Tyr, Phe, Asp, Gly,
      Pro, His, or Glu
<220> FEATURE:
<221> NAME/KEY: MOD_RES
<222> LOCATION: (30)
<223> OTHER INFORMATION: Arg, Glu, or His
<220> FEATURE:
<221> NAME/KEY: MOD_RES
<222> LOCATION: (31)
<223> OTHER INFORMATION: Lys, Arg, Thr, Ser, Glu, Asp, Trp, Tyr, Phe,
      His, Gly, or not present
<220> FEATURE:
<221> NAME/KEY: MOD_RES
<222> LOCATION: (32)
<223> OTHER INFORMATION: This residue may or may not be present; when
      present position 31 is Gly

<400> SEQUENCE: 4

Xaa Xaa Glu Gly Xaa Xaa Thr Ser Asp Xaa Ser Ser Tyr Leu Glu Xaa
1               5                   10                  15

Xaa Xaa Xaa Lys Xaa Phe Ile Xaa Trp Leu Xaa Xaa Xaa Xaa Xaa Pro
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His, beta-
      hydroxy-His, homo-His, alpha-fluoromethyl-His,
      or alpha-methyl-His
<220> FEATURE:
<221> NAME/KEY: MOD_RES
<222> LOCATION: (2)
<223> OTHER INFORMATION: Gly, Ala, Val, Leu, Ile, Ser, Met, or Thr
<220> FEATURE:
<221> NAME/KEY: MOD_RES
<222> LOCATION: (6)
<223> OTHER INFORMATION: His, Trp, Phe, or Tyr
<220> FEATURE:
<221> NAME/KEY: MOD_RES
<222> LOCATION: (10)
<223> OTHER INFORMATION: Leu, Ser, Thr, Trp, His, Phe, Asp, Val, Glu, or
      Ala
<220> FEATURE:
<221> NAME/KEY: MOD_RES
<222> LOCATION: (16)
<223> OTHER INFORMATION: Gly, Asp, Glu, Gln, Asn, Lys, Arg, or Cys
<220> FEATURE:
<221> NAME/KEY: MOD_RES
<222> LOCATION: (17)
<223> OTHER INFORMATION: His, Asp, Lys, Glu, or Gln
<220> FEATURE:
<221> NAME/KEY: MOD_RES
<222> LOCATION: (20)
```

```
<223> OTHER INFORMATION: Asp, Lys, Glu, or His
<220> FEATURE:
<221> NAME/KEY: MOD_RES
<222> LOCATION: (24)
<223> OTHER INFORMATION: Ala, Glu, Asp, Ser, or His
<220> FEATURE:
<221> NAME/KEY: MOD_RES
<222> LOCATION: (29)
<223> OTHER INFORMATION: Thr, Ser, Lys, Arg, Trp, Tyr, Phe, Asp, Gly,
      Pro, His, or Glu
<220> FEATURE:
<221> NAME/KEY: MOD_RES
<222> LOCATION: (31)
<223> OTHER INFORMATION: Lys, Arg, Thr, Ser, Glu, Asp, Trp, Tyr, Phe,
      His, Gly, or not present
<220> FEATURE:
<221> NAME/KEY: MOD_RES
<222> LOCATION: (32)
<223> OTHER INFORMATION: This residue may or may not be present; when
      present position 31 is Gly

<400> SEQUENCE: 5

Xaa Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa Pro
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His, beta-
      hydroxy-His, homo-His, alpha-fluoromethyl-His,
      or alpha-methyl-His
<220> FEATURE:
<221> NAME/KEY: MOD_RES
<222> LOCATION: (2)
<223> OTHER INFORMATION: Gly, Ala, Val, Leu, Ile, Ser, or Thr
<220> FEATURE:
<221> NAME/KEY: MOD_RES
<222> LOCATION: (16)
<223> OTHER INFORMATION: Gly, Asp, Glu, Gln, Asn, Lys, Arg, or Cys
<220> FEATURE:
<221> NAME/KEY: MOD_RES
<222> LOCATION: (17)
<223> OTHER INFORMATION: His, Asp, Lys, Glu, or Gln
<220> FEATURE:
<221> NAME/KEY: MOD_RES
<222> LOCATION: (18)
<223> OTHER INFORMATION: Ala, Glu, Asp, Ser, or His
<220> FEATURE:
<221> NAME/KEY: MOD_RES
<222> LOCATION: (24)
<223> OTHER INFORMATION: Ala, Glu, Asp, Ser, or His
<220> FEATURE:
<221> NAME/KEY: MOD_RES
<222> LOCATION: (31)
<223> OTHER INFORMATION: Lys, Arg, Thr, Ser, Glu, Asp, Trp, Tyr, Phe,
      His, Gly, or not present
<220> FEATURE:
<221> NAME/KEY: MOD_RES
<222> LOCATION: (32)
<223> OTHER INFORMATION: This residue may or may not be present; when
      present position 31 is Gly

<400> SEQUENCE: 6

Xaa Xaa Glu Gly Thr Phe Thr Ser Glu Val Ser Ser Tyr Leu Glu Xaa
1               5                   10                  15
```

```
Xaa Xaa Ala Lys Glu Phe Ile Xaa Trp Leu Val Lys Gly Arg Xaa Pro
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His, beta-
      hydroxy-His, homo-His, alpha-fluoromethyl-His,
      or alpha-methyl-His
<220> FEATURE:
<221> NAME/KEY: MOD_RES
<222> LOCATION: (2)
<223> OTHER INFORMATION: Ala, Gly, Val, Thr, Ile, or alpha-methyl-Ala
<220> FEATURE:
<221> NAME/KEY: MOD_RES
<222> LOCATION: (15)
<223> OTHER INFORMATION: Glu, Gln, Ala, Thr, Ser, or Gly
<220> FEATURE:
<221> NAME/KEY: MOD_RES
<222> LOCATION: (21)
<223> OTHER INFORMATION: Glu, Gln, Ala, Thr, Ser, or Gly

<400> SEQUENCE: 7

Xaa Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4-imidazopropionyl-Ala, 4-imidazoacetyl-Ala,
      4-imidazo-alpha-Ala, or alpha-dimethyl-acetyl-Ala
<220> FEATURE:
<221> NAME/KEY: MOD_RES
<222> LOCATION: (19)
<223> OTHER INFORMATION: Lys or Arg
<220> FEATURE:
<221> NAME/KEY: MOD_RES
<222> LOCATION: (27)
<223> OTHER INFORMATION: Lys may be branched with a C6-C10 unbranched
      acyl
<220> FEATURE:
<221> NAME/KEY: MOD_RES
<222> LOCATION: (30)
<223> OTHER INFORMATION: This residue may or may not be present
<220> FEATURE:
<223> OTHER INFORMATION: May or may not be c-term amidated

<400> SEQUENCE: 8

Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg Gly
            20                  25                  30

<210> SEQ ID NO 9
<211> LENGTH: 31
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His, beta-
      hydroxy-His, homo-His, alpha-fluoromethyl-His,
      or alpha-methyl-His
<220> FEATURE:
<221> NAME/KEY: MOD_RES
<222> LOCATION: (2)
<223> OTHER INFORMATION: Ala, Gly, Val, Leu, Ile, Ser, or Thr
<220> FEATURE:
<221> NAME/KEY: MOD_RES
<222> LOCATION: (6)
<223> OTHER INFORMATION: Phe, Trp, or Tyr
<220> FEATURE:
<221> NAME/KEY: MOD_RES
<222> LOCATION: (10)
<223> OTHER INFORMATION: Val, Trp, Ile, Leu, Phe, or Tyr
<220> FEATURE:
<221> NAME/KEY: MOD_RES
<222> LOCATION: (12)
<223> OTHER INFORMATION: Ser, Trp, Tyr, Phe, Lys, Ile, Leu, or Val
<220> FEATURE:
<221> NAME/KEY: MOD_RES
<222> LOCATION: (13)
<223> OTHER INFORMATION: Tyr, Trp, or Phe
<220> FEATURE:
<221> NAME/KEY: MOD_RES
<222> LOCATION: (14)
<223> OTHER INFORMATION: Leu, Phe, Tyr or Trp
<220> FEATURE:
<221> NAME/KEY: MOD_RES
<222> LOCATION: (16)
<223> OTHER INFORMATION: Gly, Glu, Asp, or Lys
<220> FEATURE:
<221> NAME/KEY: MOD_RES
<222> LOCATION: (19)
<223> OTHER INFORMATION: Ala, Val, Ile, or Leu
<220> FEATURE:
<221> NAME/KEY: MOD_RES
<222> LOCATION: (21)
<223> OTHER INFORMATION: Glu, Ile, or Ala
<220> FEATURE:
<221> NAME/KEY: MOD_RES
<222> LOCATION: (24)
<223> OTHER INFORMATION: Ala or Glu
<220> FEATURE:
<221> NAME/KEY: MOD_RES
<222> LOCATION: (27)
<223> OTHER INFORMATION: Val or Ile
<220> FEATURE:
<221> NAME/KEY: MOD_RES
<222> LOCATION: (31)
<223> OTHER INFORMATION: Gly, His, or not present
<220> FEATURE:
<223> OTHER INFORMATION: May or may not be c-term amidated

<400> SEQUENCE: 9

Xaa Xaa Glu Gly Thr Xaa Thr Ser Asp Xaa Ser Xaa Xaa Xaa Glu Xaa
1               5                   10                  15

Gln Ala Xaa Lys Xaa Phe Ile Xaa Trp Leu Xaa Lys Gly Arg Xaa
            20                  25                  30

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His,
      13-hydroxy-His, homo-His, alpha-fluoromethyl-His, or
      alpha-methyl-His
<220> FEATURE:
<221> NAME/KEY: MOD_RES
<222> LOCATION: (2)
<223> OTHER INFORMATION: Gly, Ala, or Val
<220> FEATURE:
<221> NAME/KEY: MOD_RES
<222> LOCATION: (10)
<223> OTHER INFORMATION: Leu or Val
<220> FEATURE:
<221> NAME/KEY: MOD_RES
<222> LOCATION: (12)
<223> OTHER INFORMATION: Lys or Ser
<220> FEATURE:
<221> NAME/KEY: MOD_RES
<222> LOCATION: (13)
<223> OTHER INFORMATION: Gln or Tyr
<220> FEATURE:
<221> NAME/KEY: MOD_RES
<222> LOCATION: (14)
<223> OTHER INFORMATION: Met or Leu
<220> FEATURE:
<221> NAME/KEY: MOD_RES
<222> LOCATION: (16)
<223> OTHER INFORMATION: Glu or Gln
<220> FEATURE:
<221> NAME/KEY: MOD_RES
<222> LOCATION: (17)
<223> OTHER INFORMATION: Glu or Gln
<220> FEATURE:
<221> NAME/KEY: MOD_RES
<222> LOCATION: (19)
<223> OTHER INFORMATION: Val or Ala
<220> FEATURE:
<221> NAME/KEY: MOD_RES
<222> LOCATION: (20)

```
<223> OTHER INFORMATION: Arg or Lys
<220> FEATURE:
<221> NAME/KEY: MOD_RES
<222> LOCATION: (21)
<223> OTHER INFORMATION: Leu or Glu
<220> FEATURE:
<221> NAME/KEY: MOD_RES
<222> LOCATION: (24)
<223> OTHER INFORMATION: Glu or Ala
<220> FEATURE:
<221> NAME/KEY: MOD_RES
<222> LOCATION: (27)
<223> OTHER INFORMATION: Val or Lys
<220> FEATURE:
<221> NAME/KEY: MOD_RES
<222> LOCATION: (28)
<223> OTHER INFORMATION: Asn or Lys
<220> FEATURE:
<221> NAME/KEY: MOD_RES
<222> LOCATION: (30)
<223> OTHER INFORMATION: Gly or Arg
<220> FEATURE:
<221> NAME/KEY: MOD_RES
<222> LOCATION: (31)
<223> OTHER INFORMATION: Gly, Pro, or not present
<220> FEATURE:
<221> NAME/KEY: MOD_RES
<222> LOCATION: (32)..(39)
<223> OTHER INFORMATION: This region may or may not be present; when
      present position 31 is Pro

<400> SEQUENCE: 12

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Gly Xaa Xaa Ser
            20                  25                  30

Ser Gly Ala Pro Pro Pro Ser
            35

<210> SEQ ID NO 13
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His,
      hydroxy-His, homo-His, alpha-fluoromethyl-His, or alpha-methyl-His
<220> FEATURE:
<221> NAME/KEY: MOD_RES
<222> LOCATION: (2)
<223> OTHER INFORMATION: Ala, Gly, Val, Leu, Ile, Ser, or Thr
<220> FEATURE:
<221> NAME/KEY: MOD_RES
<222> LOCATION: (6)
<223> OTHER INFORMATION: Phe, Trp, or Tyr
<220> FEATURE:
<221> NAME/KEY: MOD_RES
<222> LOCATION: (10)
<223> OTHER INFORMATION: Val, Trp, Ile, Leu, Phe, or Tyr
<220> FEATURE:
<221> NAME/KEY: MOD_RES
<222> LOCATION: (12)
<223> OTHER INFORMATION: Ser, Trp, Tyr, Phe, Lys, Ile, Leu, Val
<220> FEATURE:
<221> NAME/KEY: MOD_RES
<222> LOCATION: (13)
<223> OTHER INFORMATION: Tyr, Trp, or Phe
<220> FEATURE:
<221> NAME/KEY: MOD_RES
<222> LOCATION: (14)
<223> OTHER INFORMATION: Leu, Phe, Tyr, or Trp
```

```
<220> FEATURE:
<221> NAME/KEY: MOD_RES
<222> LOCATION: (16)
<223> OTHER INFORMATION: Gly, Glu, Asp, or Lys
<220> FEATURE:
<221> NAME/KEY: MOD_RES
<222> LOCATION: (19)
<223> OTHER INFORMATION: Ala, Val, Ile, or Leu
<220> FEATURE:
<221> NAME/KEY: MOD_RES
<222> LOCATION: (21)
<223> OTHER INFORMATION: Glu, Ile, or Ala
<220> FEATURE:
<221> NAME/KEY: MOD_RES
<222> LOCATION: (24)
<223> OTHER INFORMATION: Ala or Glu
<220> FEATURE:
<221> NAME/KEY: MOD_RES
<222> LOCATION: (27)
<223> OTHER INFORMATION: Val or Ile
<220> FEATURE:
<221> NAME/KEY: MOD_RES
<222> LOCATION: (28)
<223> OTHER INFORMATION: Lys, Asp, Arg, or Glu
<220> FEATURE:
<221> NAME/KEY: MOD_RES
<222> LOCATION: (30)
<223> OTHER INFORMATION: Gly, Pro, or Arg
<220> FEATURE:
<221> NAME/KEY: MOD_RES
<222> LOCATION: (31)
<223> OTHER INFORMATION: Gly, Pro, or Ser
<220> FEATURE:
<221> NAME/KEY: MOD_RES
<222> LOCATION: (32)
<223> OTHER INFORMATION: Ser, Pro, or His
<220> FEATURE:
<221> NAME/KEY: MOD_RES
<222> LOCATION: (33)
<223> OTHER INFORMATION: Ser, Arg, Thr, Trp, or Lys
<220> FEATURE:
<221> NAME/KEY: MOD_RES
<222> LOCATION: (34)
<223> OTHER INFORMATION: Ser or Gly
<220> FEATURE:
<221> NAME/KEY: MOD_RES
<222> LOCATION: (35)
<223> OTHER INFORMATION: Ala, Asp, Arg, Glu, Lys, or Gly
<220> FEATURE:
<221> NAME/KEY: MOD_RES
<222> LOCATION: (36)
<223> OTHER INFORMATION: Pro, Ala, or not present
<220> FEATURE:
<221> NAME/KEY: MOD_RES
<222> LOCATION: (37)
<223> OTHER INFORMATION: Pro, Ala, or not present
<220> FEATURE:
<221> NAME/KEY: MOD_RES
<222> LOCATION: (38)
<223> OTHER INFORMATION: Pro, Ala, Arg, Lys, His, or not present
<220> FEATURE:
<221> NAME/KEY: MOD_RES
<222> LOCATION: (39)
<223> OTHER INFORMATION: Ser, His, Pro, Lys, Arg, or not present
<220> FEATURE:
<221> NAME/KEY: MOD_RES
<222> LOCATION: (40)
<223> OTHER INFORMATION: His, Ser, Arg, Lys, or not present
<220> FEATURE:
<221> NAME/KEY: MOD_RES
<222> LOCATION: (41)
<223> OTHER INFORMATION: His, Ser, Arg, Lys, or not present
<220> FEATURE:
<223> OTHER INFORMATION: May or may not be c-term amidated
<220> FEATURE:
<223> OTHER INFORMATION: See specification as filed for detailed
      description of substitutions and preferred embodiments

<400> SEQUENCE: 13
```

```
Xaa Xaa Glu Gly Thr Xaa Thr Ser Asp Xaa Ser Xaa Xaa Xaa Glu Xaa
1               5                   10                  15

Gln Ala Xaa Lys Xaa Phe Ile Xaa Trp Leu Xaa Xaa Gly Xaa Xaa Xaa
            20                  25                  30

Xaa Xaa Xaa Xaa Xaa Xaa Xaa Xaa Xaa
        35                  40
```

<210> SEQ ID NO 14
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, d-His, desamino-His, 2-amino-His,
      beta-hydroxy-His, homo-His, alpha-fluoromethyl-His, or
      alpha-methyl-His
<220> FEATURE:
<221> NAME/KEY: MOD_RES
<222> LOCATION: (2)
<223> OTHER INFORMATION: Gly, Val, Leu, Ile, Ser, or Thr
<220> FEATURE:
<221> NAME/KEY: MOD_RES
<222> LOCATION: (10)
<223> OTHER INFORMATION: Val, Trp, Ile, Leu, Phe, or Tyr
<220> FEATURE:
<221> NAME/KEY: MOD_RES
<222> LOCATION: (16)
<223> OTHER INFORMATION: Gly, Glu, Asp, or Lys
<220> FEATURE:
<221> NAME/KEY: MOD_RES
<222> LOCATION: (19)
<223> OTHER INFORMATION: Ala, Val, Ile, or Leu
<220> FEATURE:
<221> NAME/KEY: MOD_RES
<222> LOCATION: (27)
<223> OTHER INFORMATION: Val or Ile
<220> FEATURE:
<221> NAME/KEY: MOD_RES
<222> LOCATION: (28)
<223> OTHER INFORMATION: Lys, Asp, Arg, or Glu
<220> FEATURE:
<221> NAME/KEY: MOD_RES
<222> LOCATION: (30)
<223> OTHER INFORMATION: Gly, Pro, or Arg
<220> FEATURE:
<221> NAME/KEY: MOD_RES
<222> LOCATION: (31)
<223> OTHER INFORMATION: Gly, Pro, or Ser
<220> FEATURE:
<221> NAME/KEY: MOD_RES
<222> LOCATION: (32)
<223> OTHER INFORMATION: Ser, Pro, or His
<220> FEATURE:
<221> NAME/KEY: MOD_RES
<222> LOCATION: (33)
<223> OTHER INFORMATION: Ser, Arg, Thr, Trp, or Lys
<220> FEATURE:
<221> NAME/KEY: MOD_RES
<222> LOCATION: (34)
<223> OTHER INFORMATION: Ser or Gly
<220> FEATURE:
<221> NAME/KEY: MOD_RES
<222> LOCATION: (35)
<223> OTHER INFORMATION: Ala, Asp, Arg, Glu, Lys, or Gly
<220> FEATURE:
<221> NAME/KEY: MOD_RES
<222> LOCATION: (36)
<223> OTHER INFORMATION: Pro or Ala
<220> FEATURE:
<221> NAME/KEY: MOD_RES
<222> LOCATION: (37)

```
<223> OTHER INFORMATION: Pro or Ala
<220> FEATURE:
<221> NAME/KEY: MOD_RES
<222> LOCATION: (38)
<223> OTHER INFORMATION: Pro, Ala, Arg, Lys, His, or not present
<220> FEATURE:
<221> NAME/KEY: MOD_RES
<222> LOCATION: (39)
<223> OTHER INFORMATION: Ser, His, Pro, Lys, Arg, or not present
<220> FEATURE:
<221> NAME/KEY: MOD_RES
<222> LOCATION: (40)
<223> OTHER INFORMATION: His, Ser, Arg, Lys, or not present
<220> FEATURE:
<221> NAME/KEY: MOD_RES
<222> LOCATION: (41)
<223> OTHER INFORMATION: His, Ser, Arg, Lys, or not present
<220> FEATURE:
<223> OTHER INFORMATION: May or may not be c-term amidated
<220> FEATURE:
<223> OTHER INFORMATION: See specification as filed for detailed
      description of substitutions and preferred embodiments

<400> SEQUENCE: 14

Xaa Xaa Glu Gly Thr Phe Thr Ser Asp Xaa Ser Ser Tyr Lys Glu Xaa
1               5                   10                  15

Gln Ala Xaa Lys Glu Phe Ile Ala Trp Leu Xaa Xaa Gly Xaa Xaa Xaa
            20                  25                  30

Xaa Xaa Xaa Xaa Xaa Xaa Xaa Xaa Xaa
        35                  40

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Ser Ser Gly Ala Pro Pro Pro Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 16

Gly Pro Ser Ser Gly Ala Pro Pro Pro Ser
1               5                   10
```